(12) United States Patent
Springer et al.

(10) Patent No.: US 6,465,456 B2
(45) Date of Patent: Oct. 15, 2002

(54) ISOXAZOLINONE ANTIBACTERIAL AGENTS

(75) Inventors: Dane M. Springer, North Haven, CT (US); Jason T. Goodrich, Meriden, CT (US); Zhaoxing Meng, Middletown, CT (US); Lawrence B. Snyder, Killingworth, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/893,845

(22) Filed: Jun. 28, 2001

(65) Prior Publication Data

US 2002/0040142 A1 Apr. 4, 2002

Related U.S. Application Data

(60) Provisional application No. 60/214,977, filed on Jun. 29, 2000.

(51) Int. Cl.[7] ............... A61K 31/496; A61K 31/5377; C07D 413/10; C07D 413/14; C07D 417/14

(52) U.S. Cl. ............... 514/235.8; 514/252.11; 514/252.19; 514/253.1; 514/254.03; 514/254.04; 544/121; 544/295; 544/357; 544/364; 544/367; 544/369

(58) Field of Search ................ 544/121, 295, 544/357, 364, 369, 367; 514/235.8, 252.19, 253.1, 254.03, 254.04, 252.11

(56) References Cited

U.S. PATENT DOCUMENTS

| | | | |
|---|---|---|---|
| 4,000,155 A | 12/1976 | Beck et al. | |
| 4,065,463 A | 12/1977 | Beck et al. | |
| 4,705,799 A | 11/1987 | Gregory | |
| 4,948,801 A | 8/1990 | Carlson et al. | |
| 5,130,316 A | 7/1992 | Carlson et al. | |
| 5,254,577 A | 10/1993 | Carlson et al. | |
| 5,523,403 A | 6/1996 | Barbachyn | |
| 5,708,169 A | 1/1998 | Hester, Jr. et al. | |
| 6,069,145 A | 5/2000 | Betts | |
| 6,362,189 B1 | * | 3/2002 | Hester, Jr. et al. |
| 2001/0047004 A1 | * | 11/2001 | Hester, Jr. |

FOREIGN PATENT DOCUMENTS

| | | |
|---|---|---|
| EP | 693491 A1 | 1/1996 |
| EP | 694543 A1 | 1/1996 |
| EP | 694544 A1 | 1/1996 |
| EP | 697412 A1 | 2/1996 |
| WO | WO 97/10235 | 3/1997 |
| WO | WO 97/14690 | 4/1997 |
| WO | WO 97/43280 | 11/1997 |
| WO | WO 98/07708 | 2/1998 |
| WO | WO 00/10566 | 3/2000 |

* cited by examiner

*Primary Examiner*—Emily Bernhardt
(74) *Attorney, Agent, or Firm*—David M. Morse

(57) ABSTRACT

This invention describes isoxazolinone derivatives which possess antibacterial activity and are useful in the treatment of bacterial diseases. More particularly, new isoxazolinones are provided having the general formula I

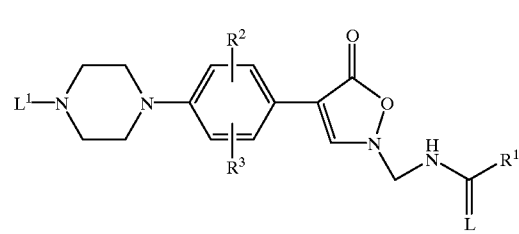

wherein $R^1$, $R^2$, $R^3$, L and $L^1$ are as described in the specification.

22 Claims, No Drawings

ISOXAZOLINONE ANTIBACTERIAL AGENTS

CROSS-REFERENCE TO RELATED APPLICATION

This application claims the benefit of U.S. Provisional Application Ser. No. 60/214,977 filed Jun. 29, 2000.

BACKGROUND OF THE INVENTION

1. Field of the Invention

The present invention is directed toward new isoxazolinones, methods for their use, and processes for their production. These novel isoxazolinone derivatives are useful as antimicrobial agents which are effective against a number of human and veterinary pathogens, including gram positive bacteria such as multiply-resistant staphylococci, streptococci, and enterococci (e.g. methicillin-resistant *Staphylococcus aureus* or vancomycin-resistant *Enterococcus faecium*).

2. Background

The literature contains a limited number of isoxazolinones used as pre-emergence herbicides. For example in U.S. Pat. No. 4,065,463, 2-methyl-4-(trifluoromethyl-m-tolyl)-3-isoxazolin-5-one and 2-methyl-4-(chloro-m-tolyl)-3-isoxazolin-5-one are disclosed as being useful in preventing the growth of weeds which have a deleterious effect on crop production.

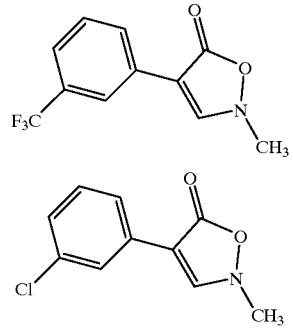

U.S. Pat. No. 4,000,155 discloses the related compound 1,2-dimethyl-4-(trifluoromethyl-m-tolyl)-3-pyrazolin-5-one for the same utility.

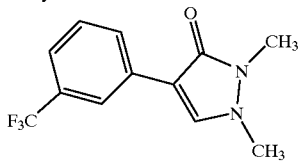

The applicants are not aware of any literature which discloses the use of these compounds as broad spectrum anti-bacterial agents. A different ring system is disclosed in WO 98/07708, which discusses the use of isoxazoline derivatives as anti-bacterial agents,

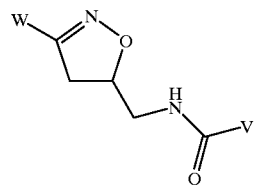

where W is a substituted aryl or heteroaryl system and V is H, or $C_1$–$C_4$ alkyl optionally substituted with F, Cl, OH, $C_1$–$C_4$ alkoxy, or acyloxy.

Oxazolidinones II shown below are a well known class of orally active antibacterial agents. The prior art contains numerous references to these compounds where Y and Z can include a wide variety of substituents. Specific substituted oxazolidinones are discussed in U.S. Pat. Nos. 4,705,799 and 5,523,403 (substituted phenyl 2-oxazolidinones), U.S. Pat. Nos. 4,948,801; 5,254,577; and 5,130,316 (arylbenzene oxazolidinyl compounds), U.S. Pat. No. 6,069,145 (piperazinophenyloxazolidinones) and European Patent Applications 0,697,412; 0,694,544; 0694,543; and 0,693,491 (5 to 9-membered heteroaryl substituted oxazolidinones).

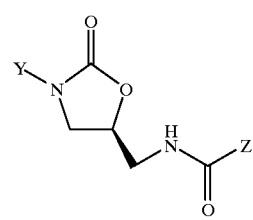

II

Additionally, certain compounds containing a substituted furanone ring have been reported to possess antibiotic activity. WO 97/14690 discloses

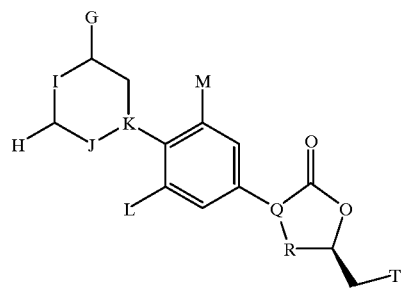

where T is hydroxy or $NHC(O)C_1$–$C_4$ alkyl, M and L are each independently hydrogen or fluoro, G and H are are each independently hydrogen or methyl, K–L is of the formula C=CH, $CHCH_2$ or $C(OH)CH_2$, I is O, SO, $SO_2$ or a substituted nitrogen, and Q–R is $CH_2$—$CH_2$ or CH=$CH_2$. Other substituted furanones are discussed in U.S. Pat. No. 5,708,169, WO 97/43280 and WO 97/10235.

Isoxazolinones of type III have been disclosed in PCT Publication WO 00/10566, but the compounds of the present invention are not disclosed or suggested in this publication.

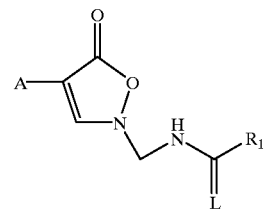

III

SUMMARY OF THE INVENTION

A first embodiment of a first aspect of the present invention is a compound of formula I

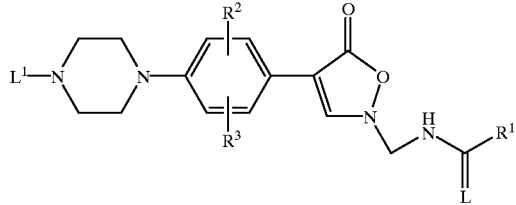

I or a pharmaceutically acceptable salt thereof, wherein:

L is oxygen or sulfur;

$L^1$ is selected from the group consisting of: $R^4$—$(CH_2)_m$—$CR^5(NR^6R^7)C(O)$—, $R^8R^9N$—$(CH_2)_n$—$C(O)$—, $C_{1-6}$alkylC(O)CH$_2$C(O)—, $R^{10}$—X—CH$_2$C(O)—, $R^{10}$—CH=CH—C(O)—, $R^{10}$—NHC(O)CH$_2$—, $R^{10}$—$(CH_2)_p$— and $R^{10}$—S(O)$_2$—;

m is 0 or an integer from 1 to 4;

n is an integer from 1 to 4;

p is an integer from 2 to 6;

X is selected from the group consisting of: a bond, sulfur, oxygen, NH and N(C$_{1-4}$alkyl);

$R^1$ is selected from the group consisting of: hydrogen, $C_{1-8}$alkyl, $C_{3-6}$cycloalkyl and $C_{1-8}$alkoxy, said $C_{1-8}$alkyl optionally substituted with one or more fluoro, chloro, hydroxy, $C_{1-8}$alkoxy or $C_{1-8}$acyloxy;

$R^2$ and $R^3$ are each independently selected from the group consisting of: hydrogen, halogen, hydroxy, nitro, amino, cyano, $C_{1-6}$alkyl, $C_{1-6}$alkoxy and trifluoromethyl;

$R^4$ is selected from the group consisting of: hydrogen, hydroxy, $C_{1-6}$thioalkoxy, imidazolyl, indolyl, —CO$_2$H and —NHC(=NH)NH$_2$;

$R^5$ is hydrogen or $C_{1-6}$alkyl; or $R^4$ and $R^5$ taken together can be —CH$_2$— when m is 1;

$R^6$ and $R^7$ are each independently selected from hydrogen or $C_{1-6}$alkyl; or $R^4$ and $R^6$ taken together can be —(CH$_2$)$_q$— when m is 1 and wherein q is 2 or 3;

$R^8$ and $R^9$ are each independently selected from hydrogen or $C_{1-6}$alkyl; or $R^8$ and $R^9$ taken together with the nitrogen to which they are attached are morpholin4-yl, piperazin-1-yl, piperidin-1-yl or —NHC(=NH)NH$_2$;

$R^{10}$ is heteroaryl, said heteroaryl selected from the group consisting of imidazolyl, benzoimidazolyl, thienyl, benzothienyl, furanyl, oxazolyl, isoxazolyl, thiazolyl, isothiazolyl, indolyl, pyridinyl, pyrimidinyl, pyrazinyl, pyrolyl, thiadiazolyl, oxadiazolyl, triazolyl, triazinyl and tetrazolyl, and said heteroaryl optionally substituted with one to three same or different amino, hydroxy, halogen, $C_{1-6}$alkyl, morpholin-4-yl, piperazin-1-yl, piperadin-1-yl, phenyl, —CO$_2$H or —CO$_2$C$_{1-6}$alkyl; and provided $R^4$ is hydrogen or $C_{1-6}$alkyl and $R^5$ is $C_{1-6}$ alkyl when m is 0.

A second embodiment of a first aspect of the present invention is a compound of the first embodiment of the first aspect and of the formula Ia

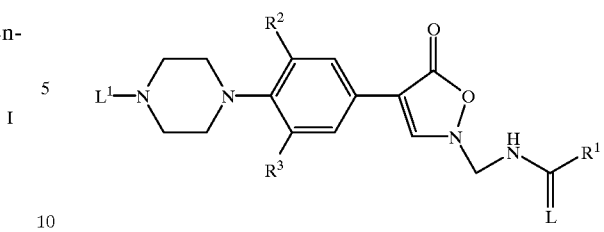

Ia or a pharmaceutically acceptable salt thereof, wherein:

L is oxygen; $R^1$ is $C_{1-8}$alkyl; and $R^2$ and $R^3$ are each independently hydrogen or halogen.

A third embodiment of a first aspect of the present invention is a compound of the second embodiment of the first aspect, or a pharmaceutically acceptable salt thereof, wherein: $R^1$ is methyl; and $R^2$ and $R^3$ are each independently hydrogen or fluoro.

A fourth embodiment of a first aspect of the present invention is compound of the third embodiment of the first aspect, or a pharmaceutically acceptable salt thereof, wherein: $R^2$ is hydrogen; $R^3$ is fluoro; and $L^1$ is $R^4$—$(CH_2)_m$—$CR^5(NR^6R^7)C(O)$— or $R^8R^9N$—$(CH_2)_n$—$C(O)$—.

A fifth embodiment of a first aspect of the present invention is a compound of the fourth embodiment of the first aspect, or a pharmaceutically acceptable salt thereof, wherein:

$L^1$ is $R^4$—$(CH_2)_m$—$CR^5(NR^6R^7)C(O)$—; $R^4$ is selected from the group consisting of hydrogen, hydroxy, thiomethoxy, 1H-imidazol-4-yl, indolyl, —CO$_2$H and —NHC(=NH)NH$_2$; $R^5$ is hydrogen or $C_{1-6}$alkyl, said $C_{1-6}$alkyl selected from the group consisting of methyl, ethyl, propyl, isopropyl and 2-methyipropyl; or $R^4$ and $R^5$ taken together can be —CH$_2$— when m is 0; $R^6$ is hydrogen or methyl; or $R^4$ and $R^6$ taken together can be —(CH$_2$)$_q$— when m is 1 and wherein q is 2 or 3; $R^7$ is hydrogen or $C_{1-6}$alkyl, said $C_{1-6}$alkyl selected from the group consisting of methyl, ethyl, propyl and isopropyl.

A sixth embodiment of a first aspect of the present invention is a compound of the fifth embodiment of the first aspect, or a pharmaceutically acceptable salt thereof, wherein: $R^4$ and $R^6$ taken together are —(CH$_2$)$_q$ wherein q is 2 or 3; and m is 1.

A seventh embodiment of a first aspect of the present invention is a compound of the fifth embodiment of the first aspect, or a pharmaceutically acceptable salt thereof, wherein: $R^4$ is hydrogen; m is 0;

$R^5$ is $C_{1-6}$alkyl, said $C_{1-6}$alkyl selected from the group consisting of methyl, ethyl, propyl, isopropyl and 2-methylpropyl; and $R^6$ and $R^7$ are each independently hydrogen or methyl.

An eighth embodiment of a first aspect of the present invention is a compound of the fifth embodiment of the first aspect, or a pharmaceutically acceptable salt thereof, wherein: $R^4$ is selected from the group consisting of hydroxy, thiomethoxy, 1H-imidazol-4-yl, —CO$_2$H and —NHC(=NH)NH$_2$; $R^5$ is hydrogen; $R^6$ and $R^7$ are hydrogen; and m is an integer from 1to 3.

A ninth embodiment of a first aspect of the present invention is a compound of the fourth embodiment of the first aspect, or a pharmaceutically acceptable salt thereof, wherein: $L^1$ is $R^8R^9N$—$(CH_2)_n$—$C(O)$—;

$R^8$ and $R^9$ are each independently selected from hydrogen or $C_{1-6}$alkyl; said $C_{1-6}$alkyl selected from the group consisting of methyl, ethyl and propyl; or $R^8$ and $R^9$ taken together with the nitrogen to which they are attached are morpholin-4-yl or —NHC(=NH)NH$_2$; and n is an integer from 1 to 3.

A tenth embodiment of a first aspect of the present invention is a compound of the third embodiment of the first aspect, or a pharmaceutically acceptable salt thereof, wherein:

$L^1$ is $C_{1-6}$alkylC(O)CH$_2$C(O)—; $R^2$ is hydrogen; and $R^3$ is fluoro.

An eleventh embodiment of a first aspect of the present invention is a compound of the third embodiment of the first aspect, or a pharmaceutically acceptable salt thereof, wherein: $L^1$ is $R^{10}$—X—CH$_2$C(O)—; X is selected from the group consisting of a bond, sulfur, oxygen and NH; $R^2$ is hydrogen; and $R^3$ is fluoro.

A twelth embodiment of a first aspect of the present invention is a compound of the eleventh embodiment of the first aspect, or a pharmaceutically acceptable salt thereof, wherein: $R^{10}$ is heteroaryl, said heteroaryl selected from the group consisting of imidazolyl, benzoimidazolyl, pyridinyl, pyrimidinyl, thiadiazolyl, thiazolyl, tetrazolyl, and triazolyl, and said heteroaryl optionally substituted with one to three same or different amino, hydroxy, $C_{1-6}$alkyl, phenyl or —CO$_2$C$_{1-6}$alkyl.

A thirteenth embodiment of a first aspect of the present invention is compound of the third embodiment of the first aspect, or a pharmaceutically acceptable salt thereof, wherein: $L^1$ is $R^{10}$—CH=CH—C(O)—; $R^2$ is hydrogen; and $R^3$ is fluoro.

A fourteenth embodiment of a first aspect of the present invention is a compound of the third embodiment of the first aspect, or a pharmaceutically acceptable salt thereof, wherein: $L^1$ is $R^{10}$—NHC(O)CH$_2$—; $R^2$ is hydrogen; and $R^3$ is fluoro.

A fifteenth embodiment of a first aspect of the present invention is a compound of the fourteenth embodiment of the first aspect, or a pharmaceutically acceptable salt thereof, wherein: $R^{10}$ is heteroaryl, said heteroaryl selected from the group consisting of triazolyl, thiadiazolyl and imidazolyl, and said heteroaryl optionally substituted with one $C_{1-6}$alkyl or morpholin-4-yl.

A sixteenth embodiment of a first aspect of the present invention is a compound of the third embodiment of the first aspect, or a pharmaceutically acceptable salt thereof, wherein: $L^1$ is $R^{10}$—(CH$_2$)$_p$—; $R^2$ is hydrogen; and $R^3$ is fluoro.

A seventeenth embodiment of a first aspect of the present invention is a compound of the sixteenth embodiment of the first aspect, or a pharmaceutically acceptable salt thereof, wherein: $R^{10}$ is pyrol-1-yl or indol-3-yl; and p is 2 or 3.

An eighteenth embodiment of a first aspect of the present invention is a compound of the third embodiment of the first aspect, or a pharmaceutically acceptable salt thereof, wherein: $L^1$ is $R^{10}$—S(O)$_2$—; and $R^2$ is hydrogen.

A nineteenth embodiment of a first aspect of the present invention is a compound of the eighteenth embodiment of the first aspect, or a pharmaceutically acceptable salt thereof, wherein: $R^{10}$ is heteroaryl, said heteroaryl selected from imidazolyl or isoxazolyl, and said heteroaryl optionally substituted with one or two $C_{1-6}$alkyl.

A twentieth embodiment of a first aspect of the present invention is a compound of the first embodiment of the first aspect, or a pharmaceutically acceptable salt thereof, selected from the group consisting of:

N-[4-(4-{4-[2-Amino-3-(1H-indol-3-yl)-propionyl]-piperazin-1-yl}-3-fluoro-phenyl)-5-oxo-5H-isoxazol-2-ylmethyl]-acetamide;

N-[4-(4-{4-[2-Amino-3-(1H-imidazol-4-yl)-propionyl]-piperazin-1-yl}-3-fluoro-phenyl)-5-oxo-5H-isoxazol-2-ylmethyl]-acetamide;

N-(4-{3-Fluoro-4-[4-(3-oxo-butyryl)-piperazin-1-yl]-phenyl}-5-oxo-5H-isoxazol-2-ylmethyl)-acetamide;

N-(4-{4-[4-(2-Amino-acetyl)-piperazin-1-yl]-3-fluoro-phenyl}-5-oxo-5H-isoxazol-2-ylmethyl)-acetamide;

N-(4-{3-Fluoro-4-[4-(2-1H-imidazol-4-yl-acetyl)-piperazin-1-yl]-phenyl}-5-oxo-5H-isoxazol-2-ylmethyl)-acetamide;

N-(4-{3-Fluoro-4-[4-(3-1H-imidazol-4-yl-acryloyl)-piperazin-1-yl]-phenyl}-5-oxo-5H-isoxazol-2-ylmethyl)-acetamide;

N-[4-(4-{4-[2-(1H-Benzoimidazol-2-ylsulfanyl)-acetyl]-piperazin-1-yl}-3-fluoro-phenyl)-5-oxo-5H-isoxazol-2-ylmethyl]-acetamide;

N-[4-(3-Fluoro-4-{4-[2-(4-methyl-4H-[1, 2, 4]triazol-3-ylsulfanyl)-acetyl]-piperazin-1-yl}-phenyl)-5-oxo-5H-isoxazol-2-ylmethyl]-acetamide;

2-[2-(4-{4-[2-(Acetylamino-methyl)-5-oxo-2,5-dihydro-isoxazol-4-yl]-2-fluoro-phenyl}-piperazin-1-yl)-2-oxo-ethylsulfanyl)-1H-imidazole-4-carboxylic acid ethyl ester;

2-(4-{4-[2-(Acetylamino-methyl)-5-oxo-2,5-dihydro-isoxazol-4-yl]-2-fluoro-phenyl}-piperazin-1-yl)-N-(1H-imidazol-2-yl)-acetamide;

N-[4-(3-Fluoro-4-{4-[2-(5-phenyl-4H-[1, 2, 4]triazol-3-ylsulfanyl)-acetyl]-piperazin-1-yl}-phenyl)-5-oxo-5H-isoxazol-2-ylmethyl]-acetamide;

N-[4-(3-Fluoro-4-{4-[2-(1-methyl-1H-imidazol-2-ylsulfanyl)-acetyl]-piperazin-1-yl}-phenyl)-5-oxo-5H-isoxazol-2-ylmethyl]-acetamide;

N-[4-(3-Fluoro-4-{4-[2-(pyrimidin-2-ylsulfanyl)-acetyl]-piperazin-1-yl}-phenyl)-5-oxo-5H-isoxazol-2-ylmethyl]-acetamide;

N-(4-{3-Fluoro-4-[4-(2-morpholin-4-yl-acetyl)-piperazin-1-yl]-phenyl}-5-oxo-5H-isoxazol-2-ylmethyl)-acetamide;

N-[4-(3-Fluoro-4-{4-[2-(5-methyl-4H-[1,2,4]triazol-3-ylsulfanyl)-acetyl]-piperazin-1-yl}-phenyl)-5-oxo-5H-isoxazol-2-ylmethyl]-acetamide;

N-[4-(4-{4-[2-(5-Amino-[1,3,4]thiadiazol-2-ylsulfanyl)-acetyl]-piperazin-1-yl}-3-fluoro-phenyl)-5-oxo-5H-isoxazol-2-ylmethyl]-acetamide;

N-[4-(3-Fluoro-4-{4-[2-([1,3,4]thiadiazol-2-ylsulfanyl)-acetyl]-piperazin-1-yl}-phenyl)-5-oxo-5H-isoxazol-2-ylmethyl]-acetamide;

N-[4-(3-Fluoro-4-{4-[2-(4H-[1,2,4]triazol-3-ylsulfanyl)-acetyl]-piperazin-1-yl}-phenyl)-5-oxo-5H-isoxazol-2-ylmethyl]-acetamide;

N-[4-(3-Fluoro-4-{4-[2-(thiazol-2-ylsulfanyl)-acetyl]-piperazin-1-yl}-phenyl)-5-oxo-5H-isoxazol-2-ylmethyl]-acetamide;

N-[4-(3-Fluoro-4-{4-[2-(1-methyl-1H-tetrazol-5-ylsulfanyl)-acetyl]-piperazin-1-yl}-phenyl)-5-oxo-5H-isoxazol-2-ylmethyl]-acetamide;

N-[4-(3-Fluoro-4-{4-[2-(1H-imidazol-2-ylsulfanyl)-acetyl]-piperazin-1-yl}-phenyl)-5-oxo-5H-isoxazol-2-ylmethyl]-acetamide;

2-(4-{4-[2-(Acetylamino-methyl)-5-oxo-2,5-dihydro-isoxazol-4-yl]-2-fluoro-phenyl}-piperazin-1-yl)-N-[1,3, 4]thiadiazol-2-yl-acetamide;

N-[4-(3-Fluoro-4-{4-[2-(5-methyl-[1,3,4]thiadiazol-2-ylsulfanyl)-acetyl]-piperazin-1-yl}-phenyl)-5-oxo-5H-isoxazol-2-ylmethyl]-acetamide;

N-[4-(3-Fluoro-4-{4-[2-(5-hydroxy-4-methyl-4H-[1,2,4]triazol-3-ylsulfanyl)-acetyl]-piperazin-1-yl}-phenyl)-5-oxo-5H-isoxazol-2-ylmethyl]-acetamide;

N-[4-(3-Fluoro-4-{4-[2-(6-methyl-pyridin-3-yloxy)-acetyl]-piperazin-1-yl}-phenyl)-5-oxo-5H-isoxazol-2-ylmethyl]-acetamide;

N-(4-{4-[4-(3,5-Dimethyl-isoxazole-4-sulfonyl)-piperazin-1-yl]-3-fluoro-phenyl}-5-oxo-5H-isoxazol-2-ylmethyl)-acetamide;

N-(4-{4-[4-(1,2-Dimethyl-1H-imidazole-4-sulfonyl)-piperazin-1-yl]-3-fluoro-phenyl}-5-oxo-5H-isoxazol-2-ylmethyl)-acetamide;

N-(4-{3-Fluoro-4-[4-(1-methyl-1H-imidazole-4-sulfonyl)-piperazin-1-yl]-phenyl}-5-oxo-5H-isoxazol-2-ylmethyl)-acetamide;

N-(4-{4-[4-(1-Methyl-1H-imidazole-4-sulfonyl)-piperazin-1-yl]-phenyl}-5-oxo-5H-isoxazol-2-ylmethyl)-acetamide;

N-(4-{3-Fluoro-4-[4-(3-pyrrol-1-yl-propyl)-piperazin-1-yl]-phenyl}-5-oxo-5H-isoxazol-2-ylmethyl)-acetamide; and N-[4-(3-Fluoro-4-{4-[2-(1H-indol-3-yl)-ethyl]-piperazin-1-yl}-phenyl)-5-oxo-5H-isoxazol-2-ylmethyl]-acetamide.

A first embodiment of a second aspect of the present invention is a pharmaceutical composition comprising a compound of any of the first through twentieth embodiments of the first aspect in admixture with a pharmaceutically acceptable adjuvant, diluent or carrier.

A first embodiment of a third aspect of the present invention is a method of treating a bacterial infection in a mammal which comprises administering a therapeutically effective amount of a compound of any of the first through twentieth embodiments of the first aspect to a mammal in need thereof.

The compounds of this invention are structurally distinct from the previously reported oxazolidinone, isoxazoline and isoxazolinone antibiotics. The compounds of formula I are antibacterial agents useful in the treatment of infections in humans and other animals caused by a variety of bacteria, particularly methicillin-resistant *Staphylococcus aureus* and vancomycin-resistant *Enterococcus faecium*.

Also included in the invention are processes for preparing the compounds of formula I and pharmaceutical compositions containing said compounds in combination with pharmaceutically acceptable carriers or diluents.

DETAILED DESCRIPTION

The term "pharmaceutically acceptable salt" as used herein is intended to include the non-toxic acid addition salts with inorganic or organic acids, e.g. salts with acids such as hydrochloric, phosphoric, sulfuric, maleic, acetic, citric, succinic, benzoic, fumaric, mandelic, p-toluene-sulfonic, methanesulfonic, ascorbic, lactic, gluconic, trifluoroacetic, hydroiodic, hydrobromic, and the like. These salts may be in hydrated form.

The terms "halo" or "halogen" includes chloro, bromo, fluoro and iodo, and is preferably chloro or fluoro.

The aliphatic "alkyl" groups as used herein means straight or branched chains having the specified number of carbon atoms, e.g. in the case of $C_{1-6}$ alkyl, the alkyl group may have from 1 to 6 carbon atoms. Examples of such groups include methyl, ethyl, propyl, isopropyl, butyl, isobutyl, sec-butyl, tert-butyl, n-pentyl, n-hexyl, etc. Similarly, "thioalkoxy" refers to a group of the formula —SR where R is an alkyl radical as defined above.

The term "alkoxy" alone or in combination means an alkyl ether radical where the alkyl portion is as defined above, e.g. methoxy, ethoxy, n-propoxy, isopropoxy, n-butoxy, iso-butoxy, sec-butoxy, tert-butoxy, and the like.

The term "cycloalkyl" means a saturated monocyclic hydrocarbon radical having the designated number of carbon ring members, e.g. cyclopropyl, cyclolbutyl, cyclopentyl and cyclohexyl. Similarly, the term "cycloalkenyl" means an unsaturated monocyclic hydrocarbon radical having the designated number of carbon ring members and at least one double bond.

"Heteroaryl" as used herein refers to an aromatic heterocyclic moiety having one or more atoms selected from oxygen, nitrogen or sulfur. Such ring systems include, but are not limited to, pyridinyl, thienyl, furanyl, pyrimidinyl, 2-pyridinyl, 3-pyridinyl, 4-pyridinyl, 2-pyrimidinyl, 4-pyrimidinyl, 5-pyrimidinyl, 3-pyridazinyl, 4-pyridazinyl, 3-pyrazinyl, 2-quinolyn, 3-quinolyn, 1-isoquinolyl, 3-isoquinolyl, 2-imadazolyl, 4-imadazolyl, 3-isoxazolyl, 4-isoxazolyl, 5-isoxazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-indolyl, 3-indolyl, 3-indazolyl, 2-benzoxazolyl, 2-benzothiazolyl, 2-furanyl, 3-furanyl, 2-thienyl, 3-thienyl, 2-pyrrolyl, 3-pyrrolyl, 1,2,4-oxadiazol-3-yl, 1,2,4-oxadiazol-5-yl, 1,2,4-thiadiazol-3-yl, 1,2,4-thiadiazol-5-yl, 1,2,4-thiazol-3-yl, 1,2,4-thiazol-5-yl, 1,2,3,4-tetrazol-5-yl, 5-oxazolyl, 1-pyrrolyl, 1-pyrazolyl, 1,2,3-triazol-1-yl, 1,2,4-triazol-1-yl, 1-tetrazolyl, 1-indolyl, 1-indazolyl, 2-isoindolyl, 1-purinyl, 3-isothiazolyl, 4-isothiazolyl, and 5-isothiazolyl.

Some specific preferred embodiments of the present invention are listed in the table below.

| Compound | Structure | MS Data | Preparative Method |
|---|---|---|---|
| 1 | 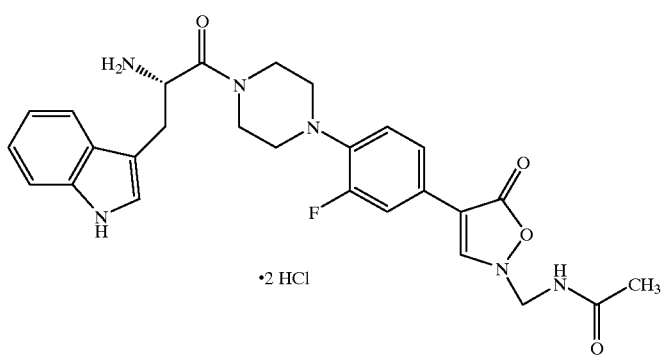 | (M + H) += 521 ESI | Method of Example 1 |

-continued

| Compound | Structure | MS Data | Preparative Method |
|---|---|---|---|
| 2 | (structure, •2 HCl) | (M + H) += 472 ESI | Method of Example 2 |
| 3 | (structure) | (M + H) += 419 ESI | Method of Example 3 |
| 4 | (structure, •2 HCl) | (M + H) += 392 ESI | Method of Example 4 |
| 5 | (structure) | (M + H) += 443 ESI | Method of Example 5 |

-continued

| Compound | Structure | MS Data | Preparative Method |
|---|---|---|---|
| 6 | 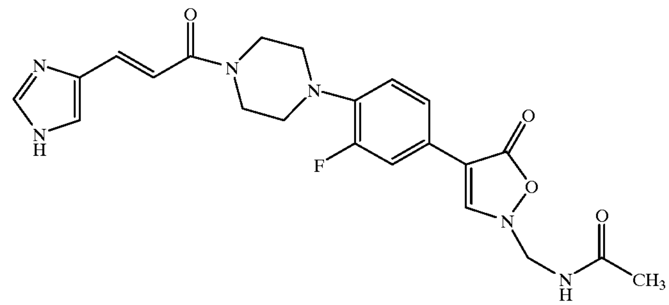 | (M + H) += 455 ESI | Method of Example 5 |
| 7 | 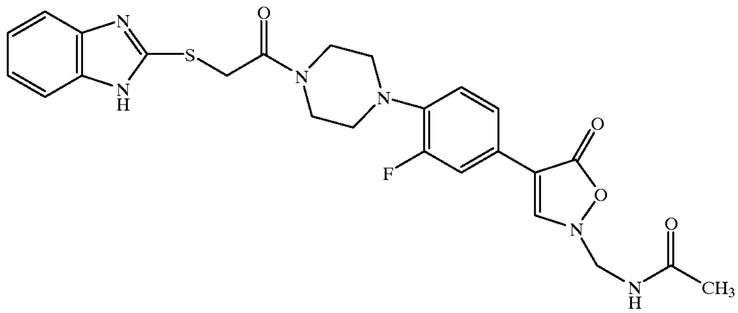 | (M + H) += 525 ESI | Method of Example 8 |
| 8 | 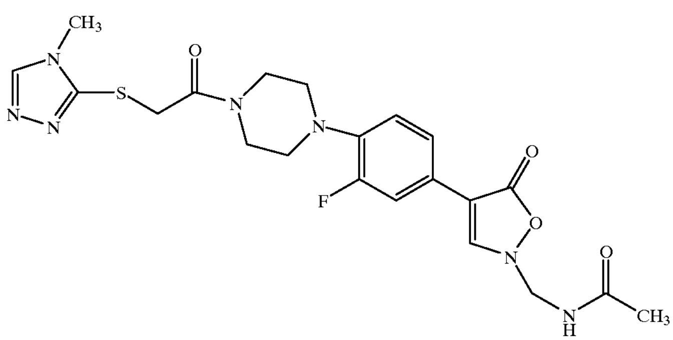 | (M + H) += 490 ESI | Method of Example 8 |
| 9 | 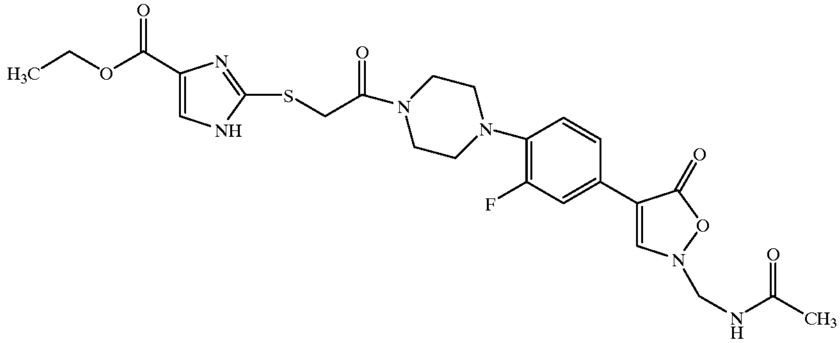 | (M + H) += 547 ESI | Method of Example 8 |

-continued

| Compound | Structure | MS Data | Preparative Method |
|---|---|---|---|
| 10 | 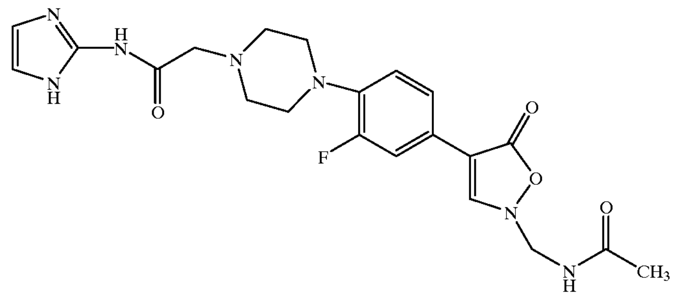 | (M + H) += 458 ESI | Method of Example 6 |
| 11 | 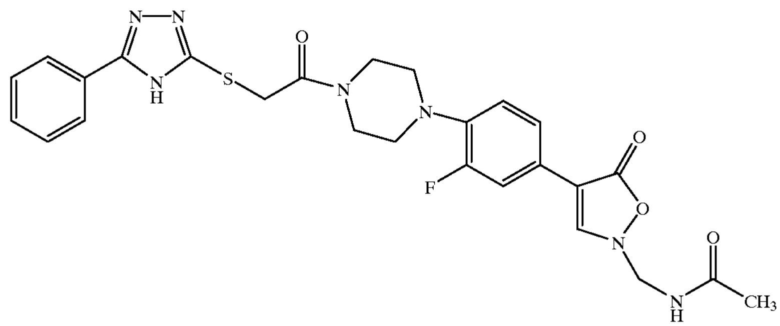 | (M + H) += 552 ESI | Method of Example 8 |
| 12 | 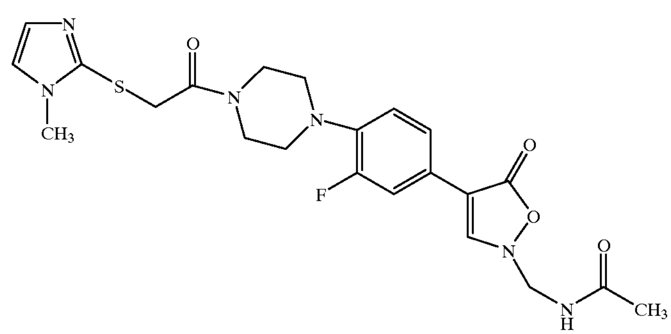 | (M + H) += 489 ESI | Method of Example 8 |
| 13 | 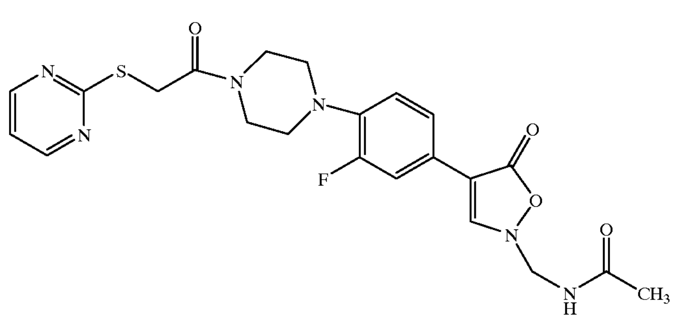 | (M + H) += 487 ESI | Method of Example 8 |

-continued

| Compound | Structure | MS Data | Preparative Method |
|---|---|---|---|
| 14 | 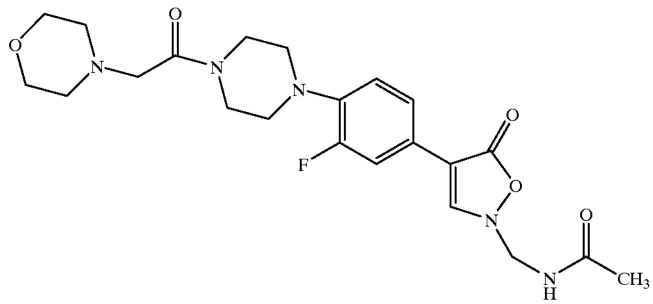 | (M + H) += 462 ESI | Method of Example 7 |
| 15 | 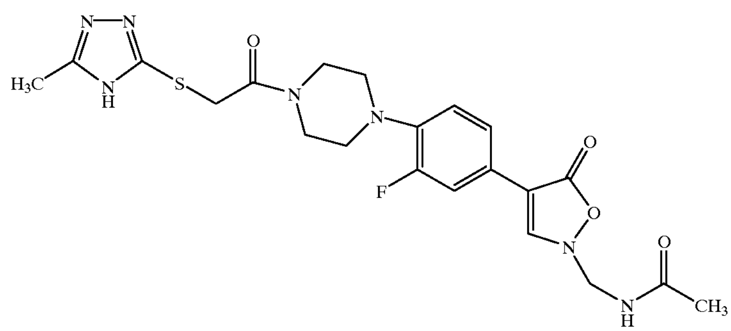 | (M + H) += 490 ESI | Method of Example 8 |
| 16 | 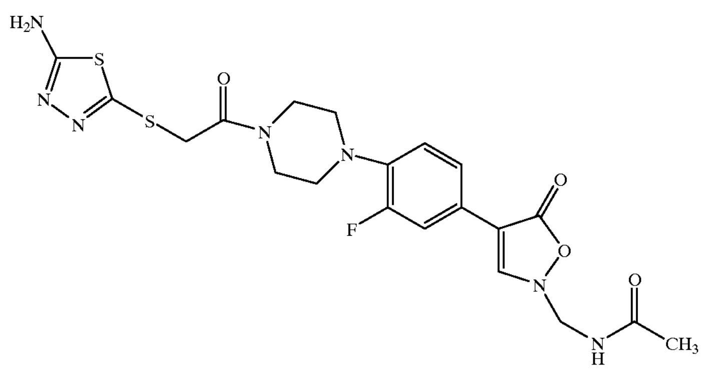 | (M + H) += 508 ESI | Method of Example 8 |
| 17 | 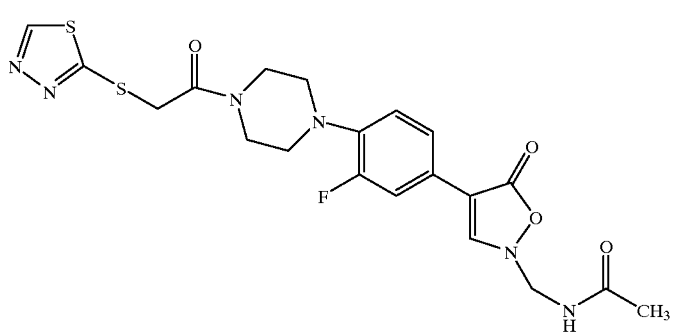 | (M + H) += 493 ESI | Method of Example 8 |

-continued
| Compound | Structure | MS Data | Preparative Method |
|---|---|---|---|
| 18 | 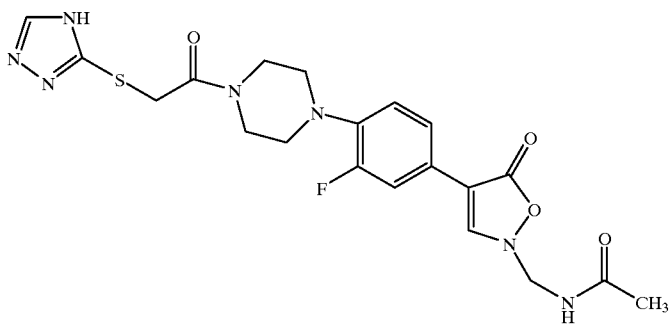 | (M + H) += 476 ESI | Method of Example 8 |
| 19 | 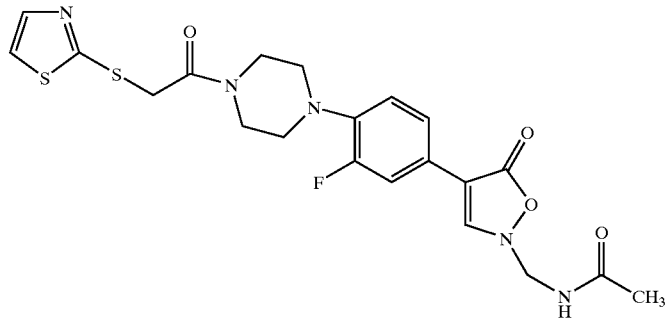 | (M + H) += 492 ESI | Method of Example 8 |
| 20 | 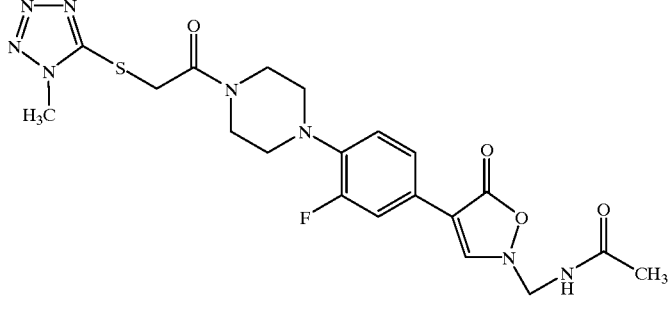 | (M + H) += 491 ESI | Method of Example 8 |
| 21 | 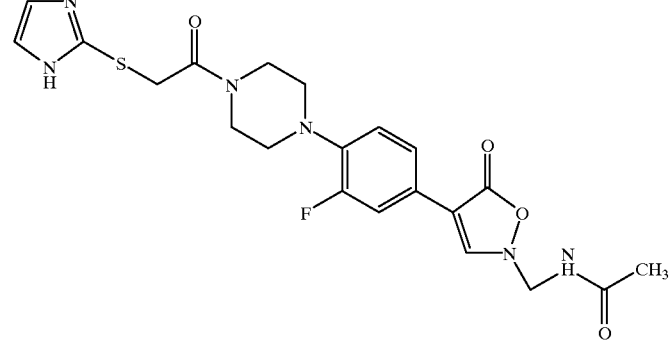 | (M + H) += 475 ESI | Method of Example 8 |

-continued

| Compound | Structure | MS Data | Preparative Method |
|---|---|---|---|
| 22 | 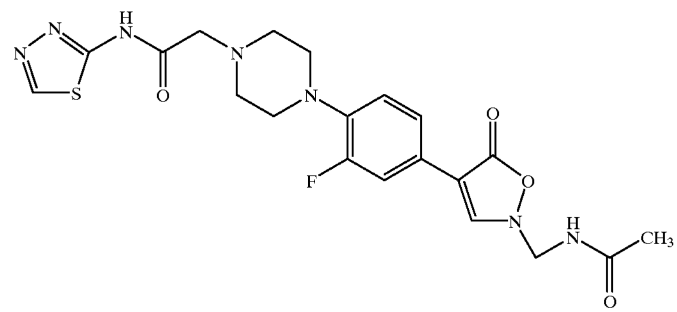 | (M + H) += 476 ESI | Method of Example 9 |
| 23 | 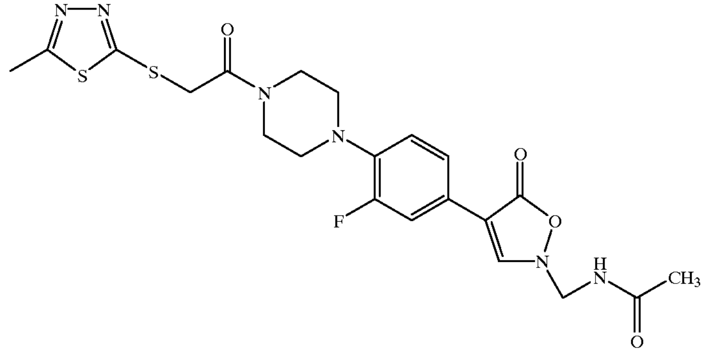 | (M + H) += 507 ESI | Method of Example 8 |
| 24 | 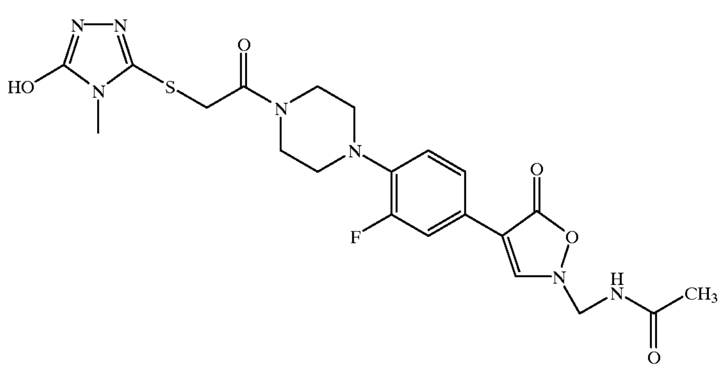 | (M + H) += 506 ESI | Method of Example 8 |
| 25 | 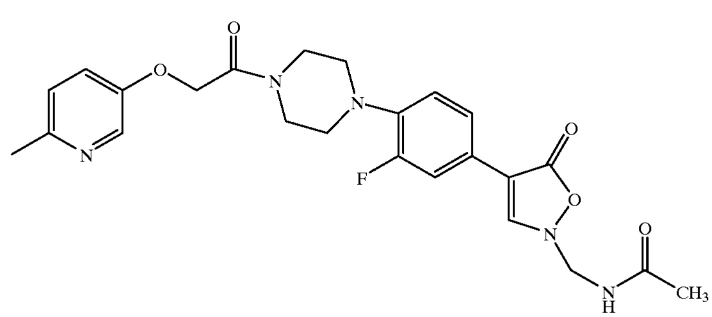 | (M + H) += 484 ESI | Method of Example 10 |

| Compound | Structure | MS Data | Preparative Method |
|---|---|---|---|
| 26 | 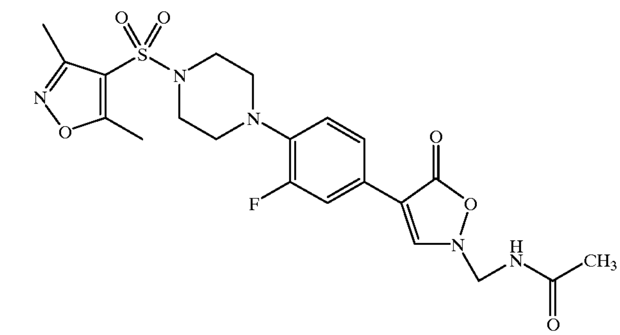 | (M + H) += 494 ESI | Method of Example 11 |
| 27 | 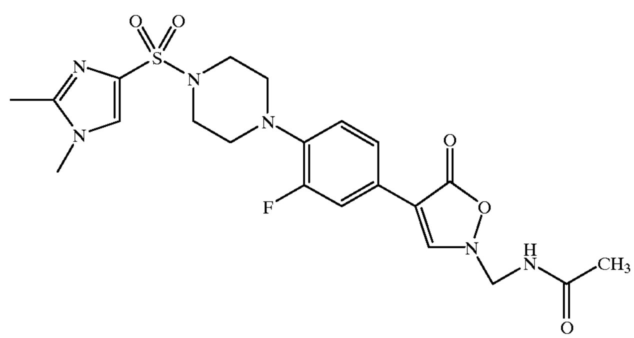 | (M + H) += 493 ESI | Method of Example 12 |
| 28 | 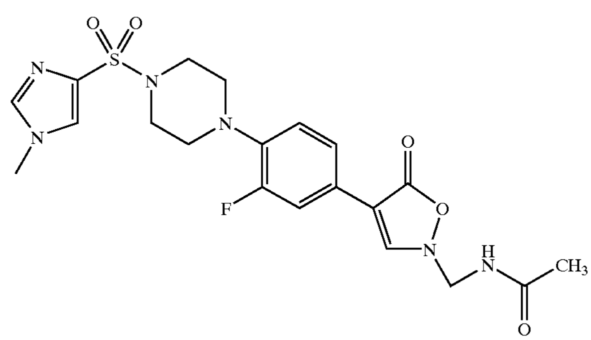 | (M + H) += 479 ESI | Method of Example 12 |
| 29 | 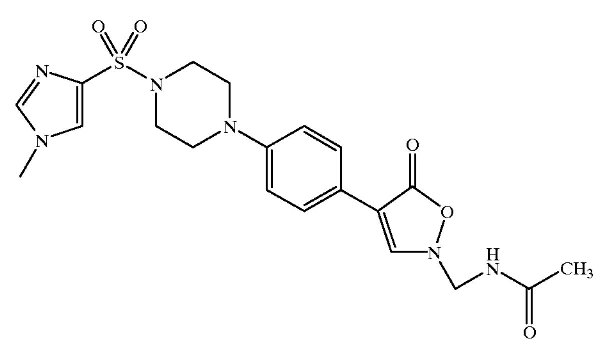 | (M + H) += 461 ESI | Method of Example 12 |

| Compound | Structure | MS Data | Preparative Method |
|---|---|---|---|
| 30 | 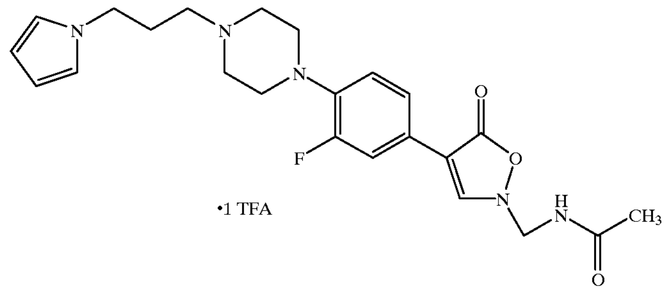 | (M + H) += 442 ESI | Method of Example 13 |
| 31 | 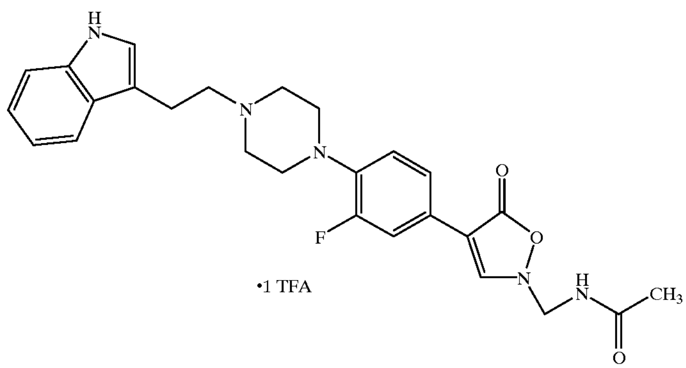 | (M + H) += 478 ESI | Method of Example 14 |

The compounds of the present invention can be made by the methods summarized below. It will be apparent to those skilled in the art that the procedures described herein are representative in nature and that alternative procedures are feasible.

The synthesis of amide-linked piperazines of type 35 and 36 is illustrated in Scheme 1. Piperazine trifluoroacetic acid salts of type 32 can be synthesized according to the methods described by Snyder and Zheng International Patent Application WO 00/10566). In situ formation of the free base of 32, and subsequent treatment with bromoacetyl chloride affords intermediates 34. Substitution of the bromine by amines of formula R'R"NH (in which R'R"NH represents amines such as $R^8R^9NH$, $R^{10}NH_2$ or $R^{10}NHC_{1-6}$alkyl), or, thiols, such as those of general formula $R^{10}SH$, alcohols of general formula $R^{10}OH$, or phenols gives products of type 35 and 36.

Scheme 1

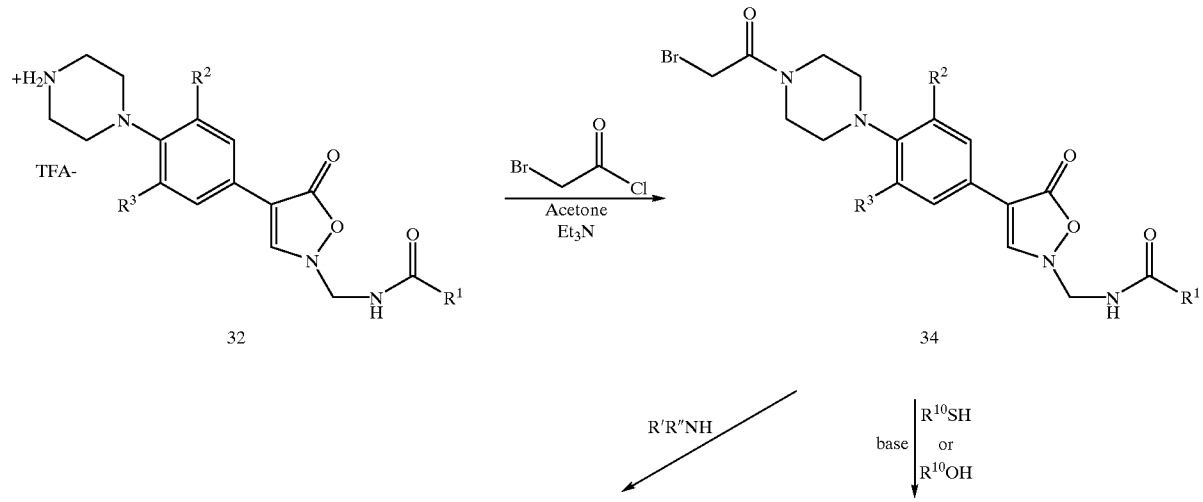

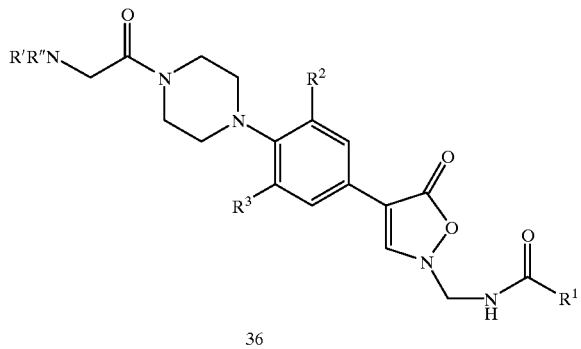

36

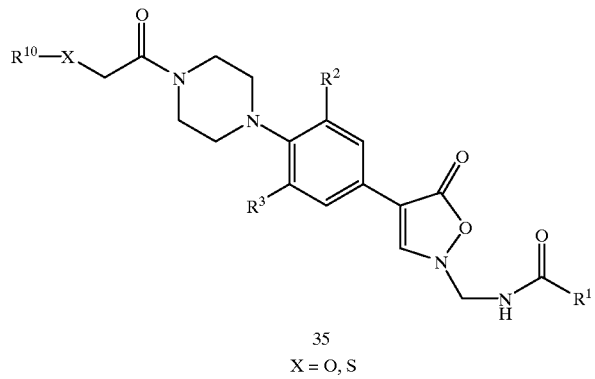

35
X = O, S

An additional method to synthesize piperazine amide derivatives of type 37 from trifluoroacetic acid salts of type 32 is depicted in Scheme 2. The amine salt 32 and a suitable carboxylic acid (in which $RCO_2H$ may represent suitable acids such as $R^4$—$(CH_2)_m$—$CR^5(NR^6R^7)C(O)OH$, $R^8R^9N$—$(CH_2)_n$—$C(O)OH$, $C_{1-6}alkylC(O)CH_2C(O)OH$, $R^1$—X—$CH_2C(O)OH$ or $R^{10}$—CH=CH—C(O)OH) are coupled using 1-(3-dimethylaminopropyl)-3-ethylcarbodiimide hydrochloride (EDC) with conditions well known to those skilled in the art to provide amides 37.

Scheme 2

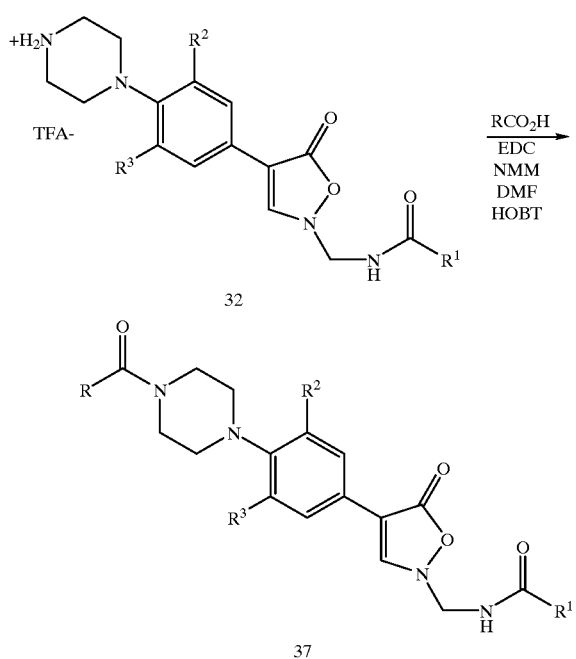

Amide derivatives of type 40 can be synthesized according to the method of Scheme 3. Amine salt 32 is converted to the free base in situ, and is then alkylated with t-butyl bromoacetate to yield esters 38. Cleavage of the t-butyl ester with trifluoroacetic acid (TFA) provides carboxylic acid intermediate 39. Coupling of 39 with amines, such as $R^{10}NH_2$, or ammonium salts using EDC provides amides 40.

Scheme 3

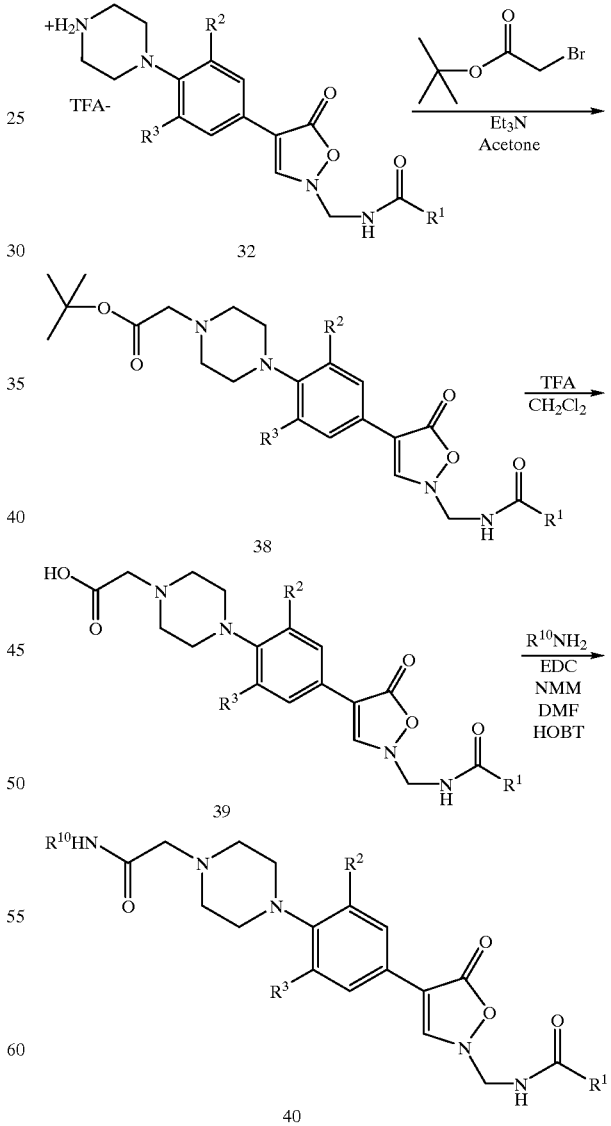

The free amine 41 can be utilized as starting material for synthesis of new isoxazolinone derivatives as depicted in Scheme 4 and Scheme 5. Coupling of 41 with various carboxylic acids (Scheme 4) using dicyclohexylcarbodiimide (DCC) or acid chlorides (using standard conditions known to those skilled in the art) serves to produce amides of type 37. Treatment of 41 with sulfonyl chlorides leads to sulfonamides 43. The reaction of amine 41 with various aldehydes utilizing reductive amination conditions well known in the art, exemplified by Pae et al. (*Bioorg. Med. Chem. Lett.* 1999, 9, 2679), leads to alkyl piperazines of type 42. Alkyl piperazines 42 can also be accessed by direct alkylation of amine 41 with substituted alkyl halides or sulfonates 44, many of which are commercially available. Alkyl halides or sulfonates 44 can also be easily synthesized according to the methods of Fries et aL (*J. Med. Chem.* 1979, 22, 356), Nordlander et al. (*Zh. Org. Khim.* 1996, 32 (12) 1883) or Geminer et al. (*Bioorg. Med. Chem. Lett.* 1993, 3 (8), 1477), or by numerous additional methods well known to those skilled in the art.

Scheme 4

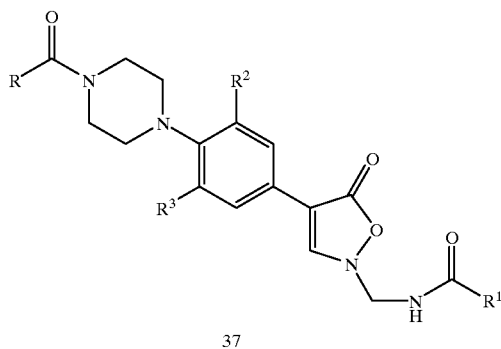

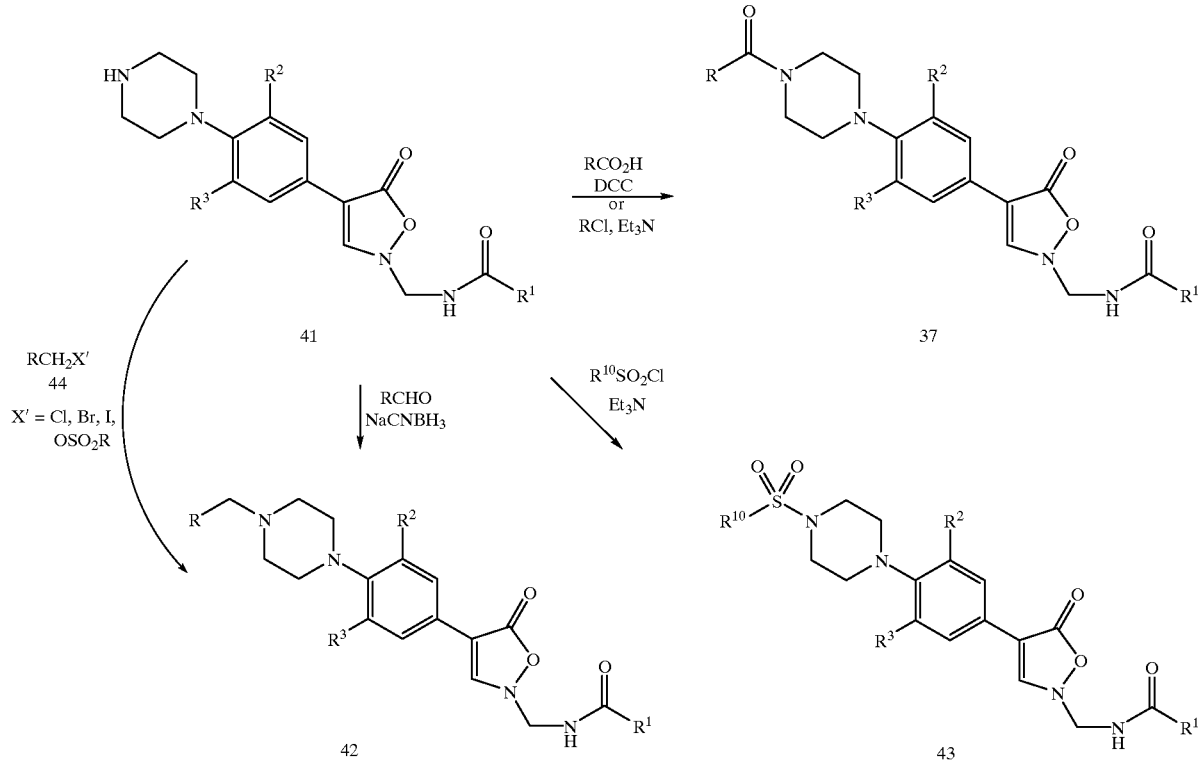

An additional method to produce piperazine derivatives of type 37 is illustrated by Scheme 5. Direct acylation of amine 41 with lactones, esters or anhydrides in an appropriate solvent, using conditions well known to those skilled in the art, affords piperazines 37.

Scheme 5

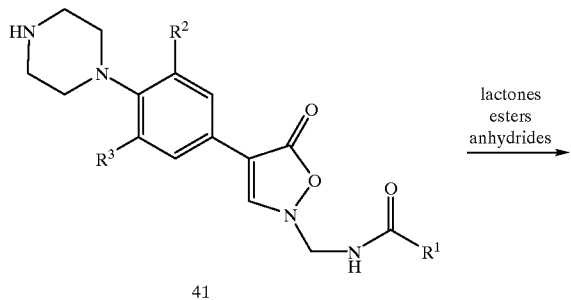

It will be understood that where the substituent groups used in the above reactions contain certain reaction-sensitive functional groups which might result in undesirable side-reactions, such groups may be protected by conventional protecting groups known to those skilled in the art. Suitable protecting groups and methods for their removal are illustrated in *Protective Groups in Organic Synthesis,* 3rd Ed., Theodora W. Greene, and Peter G. M. Wuts (John Wiley & Sons, 1999). It is intended that such protected intermediates and end-products are included within the scope of the present invention and claims.

Some of the desired end-products of formula I contain an amine. In these cases the final product may be isolated as a pharmaceutically acceptable acid addition salt by addition of an appropriate acid such as HCl, HBr, HI, or methanesulonic acid, etc. It is intended that such salts are included within the scope of the present invention and claims.

It will be appreciated that certain products within the scope of formula I may have substituent groups which can result in optical isomers. It is intended that the present invention include within its scope all such optical isomers as well as epimeric mixtures thereof (i.e., R-, S-, or racemic forms).

The compounds of the present invention are useful because they possess pharmacological activities in animals, including particularly mammals and most particularly humans. The novel compounds of formula I, or pharmaceutically acceptable salts or prodrugs thereof, are potent antibiotics active against Gram-positive bacteria. While they may be used in animal feed as additives for the promotion of growth, as preservatives for food, as bactericides in industrial applications, for example in water-based paint and in the white water of paper mills to inhibit the growth of harmful bacteria, and as disinfectants for destroying or inhibiting the growth of harmful bacteria on medical and surgical equipment, they are especially useful in the treatment of bacterial infections in humans and other animals caused by Gram-positive bacteria sensitive to the new derivatives.

The pharmaceutically active compounds of this invention may be used alone or formulated as pharmaceutical compositions comprising, in addition to the active isoxazolinone ingredient, a pharmaceutically acceptable carrier or diluent. The compound may be administered by a variety of means, for example orally, topically, or parentally (intravenous or intramuscular injection). The pharmaceutical compositions may be in solid form such as capsules, tablets, powders, etc., or in liquid form such as solutions, suspensions, or emulsions. Compositions for injection may be prepared in unit dose form in ampules or in multi-dose containers and may contain additives such as suspending, stabilizing, and dispersing agents. The compositions may be in ready-to-use form or in powder form for reconstitution at the time of delivery with a suitable vehicle such as sterile water.

Thus, according to another aspect of the invention, there is provided a method of treating a bacterial infection which comprises administering a therapeutically effective amount of the compound to a host, particularly a mammalian host, and most particularly a human patient. The use of the compounds of the present invention as pharmaceuticals and the use of the compounds of the invention in the manufacture of a medicament for the treatment of bacterial infections are also provided.

The dosage to be administered depends, to a large extent, on the particular compound being used, the particular composition formulated, the route of administration, the nature and condition of the host and the particular situs and organism being treated. Selection of the particular preferred dosage and route of application, then, is left to the discretion of the physician or veterinarian. In general, however, the compounds may be administered parentally or orally to mammalian hosts in an amount of from 25 mg/day to 2 g/day.

In Vitro Activity

Samples of the compounds prepared below in Examples 1–6 after solution in water and nutrient broth were found to exhibit the following ranges of Minimum Inhibitory Concentrations (MICs) versus the indicated microorganisms as determined by tube dilution. The MICs were determined using a broth micro dilution assay in accordance with that recommended by the National Committee for Clinical Laboratory Standards (NCCLS). Mueller-Hinton medium was used except for Staphylococci which was treated in Todd Hewitt broth. The final bacterial inoculate contained approximately $5 \times 10^5$ cfu/mL and the plates were incubated for 18 hours at 35° C. in ambient air (Streptococci in 5% $CO_2$). The MIC was defined as the lowest drug concentration that prevented visible growth.

| Microorganism | MIC value in µg/mL |
|---|---|
| S. pneumoniae A9585 | ≦8 |
| E. faecalis A20688 | ≦16 |
| S. aureus A15090, penicillinase positive | ≦16 |

Illustrative Examples

The following examples illustrate the invention, but are not intended as a limitation thereof. The abbreviations used in the examples are conventional abbreviations well known to those skilled in the art. Some of the abbreviations used are as follows:

| | |
|---|---|
| H = | hours |
| mol = | mole(s) |
| mmol = | millimole(s) |
| g = | gram(s) |
| min = | minute(s) |
| rt = | room temperature |
| THF = | tetrahydrofuran |
| L = | liter |
| mL = | milliliter(s) |
| $Et_2O$ = | diethyl ether |
| EtOAc = | ethyl acetate |
| $CH_2Cl_2$ = | methylene chloride |
| MeOH = | methanol |
| DMF = | dimethylformamide |
| BOC = | t-butoxycarbonyl |
| DCC = | dicyclohexylcarbodiimide |
| TFA = | trifluoroacetic acid |
| NMM = | N-methylmorpholine |
| EDC = | 1-(3-dimethylaminopropyl)-3-ethylcarbodiimide hydrochloride |
| HOBT = | hydroxy benzotriazole |

In the following examples all temperatures are given in degrees Celsius. All reactions are performed under nitrogen atmosphere, with commercially available anhydrous reagent grade solvent unless otherwise indicated. Proton nuclear magnetic resonance ($^1$H-NMR) spectra were recorded on a Bruker AM-300 or a Varian Gemini 300 spectrometer. All spectra were determined in $CDCl_3$, DMSO-$d_6$, $CD_3OD$, or $D_2O$ unless otherwise indicated. Chemical shifts are reported in δ units relative to tetramethylsilane (TMS) or a reference solvent peak, and interproton coupling constants are reported in Hz. Splitting patterns are designated as follows: s, singlet; d, doublet; t, triplet; q, quartet; m, multiplet; br, broad peak; dd, doublet of doublets; dt, doublet of triplets; and app d, apparent doublet, etc. Mass spectra were recorded on a Kratos MS-50, a Finnegan 4500, or a Micromass Electron-Spray spectrometer; using direct chemical ionization (DCI), or electron-spray ionization (ESI).

Analytical thin-layer chromatography (TLC) was performed using precoated silica gel plates (60F-254) and visualized by UV light, iodine vapors, or dipping in a 5% solution of phosphomolybdic acid in ethanol. Column chromatography (also referred to as flash chromatography) was performed using 260–400 mesh silica gel from E-Merck at pressures somewhat above atmospheric pressure with the indicated solvents for elution of compounds.

EXAMPLE 1

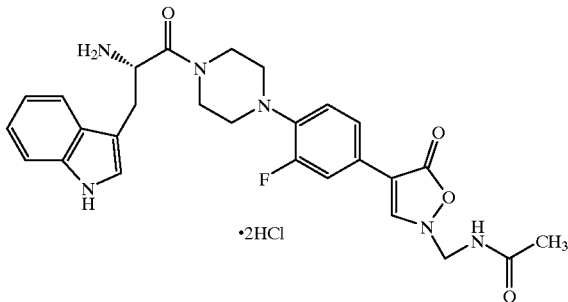

Synthesis of intermediate 41 and compound 1

A. Amine salt 32 ($R^3$=F, $R^2$=H, $R^1$=$CH_3$; 5.18 g, 11.6 mmol) is partitioned between 150 mL 25% methanol/chloroform and 50 ml half-saturated aqueous sodium bicarbonate solution. The organic layer is then washed with brine, dried (MgSO$_4$), and evaporated to afford amine 41 ($R^3$=F, $R^2$=H, $R^1$=$CH_3$; 2.57 g, 7.69 mmol). $^1$H-NMR (300 MHz, DMSO-d$_6$) δ 8.95–8.88 (m, 2H), 7.59–7.50 (m, 2H), 7.02 (dd, $J_{H-H}$=9 Hz, $J_{H-F}$=9 Hz, 1H), 5.0 (d, J=7 Hz, 2H), 2.97–2.90 (m, 4H), 2.90–2.81 (m, 4H).

B. Amine 41 ($R^3$=F, $R^2$=H, $R^1$=$CH_3$; 0.200 g, 0.599 mmol) is dissolved in 0.8 mL THF. BOC-L-tryptophan-BOC—OH (0.242 g, 0.599 mmol) is added followed by DCC (0.130 g, 0.630 mmol), and the reaction is stirred at rt for 1.5 h. The reaction is diluted with 3 mL of THF and 1.5 mL of ether. The insoluble material is filtered off, and the filtrate is evaporated to yield a foam. This material is dissolved in ~1 mL of ~5% methanol/CH$_2$Cl$_2$ and triturated with ether and pentane. The solid is collected by filtration to afford compound 1 as the bis-BOC protected derivative (0.272 g, 0.378 mmol). $^1$H-NMR (300 MHz, DMSO-d$_6$) δ 8.96–8.89 (m, 2H), 8.01 (d, J=8 Hz, 1H), 7.64 (d, J=8 Hz), 7.61–7.50 (m, 3H), 7.37–7.23 (m, 3H), 6.88 (dd, $J_{H-H}$=9 Hz, $J_{H-F}$=9 Hz, 1H), 5.01 (d, J=7 Hz, 2H), 4.73 (m, 1H), 3.70–3.45 (m, 4H), 3.10–2.80 (m, 4H), 1.83 (s, 3H), 1.58 (s, 9H), 1.34 (s, 9H).

C. Bis-BOC 1 obtained as above (0.223 g, 0.310 mmol), is dissolved in 2 mL methylene chloride and 1.5 mL trifluoroacetic acid is added. The reaction is stirred at rt for 45 min, and is then evaporated to dryness. The material is dissolved in 2 mL methanol and 1.2 mL 1N HCl is added, and the mixture is stirred at rt for 30 min. The mixture is evaporated to dryness, and the crude material triturated with methanol and diethyl ether to afford compound 1·2HCl (0.185 g, quant.). $^1$H-NMR (300 MHz, DMSO-d$_6$, partial) δ 8.97–8.92 (m, 2H), 8.39–8.24 (m, 3H), 7.60–7.47 (m, 3H), 7.39–7.25 (m, 2H), 7.15–7.00 (m, 1H), 6.90–6.71 (m, 1H), 5.01 (d, J=7 Hz, 2H), 4.90–4.55 (m, 4H), 3.63–3.10 (m, 4H), 2.98–2.70 (m, 2H), 1.85 (s, 3H).

EXAMPLE 2

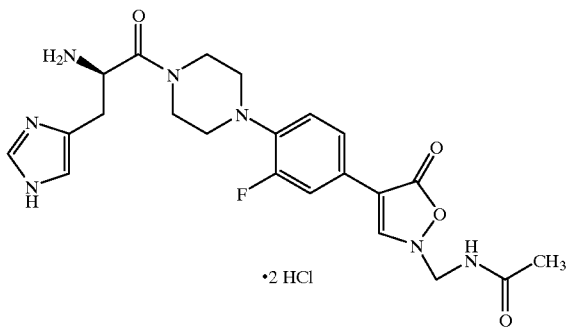

Synthesis of compound 2

Amine 41 ($R^3$=F, $R^2$=H, $R^1$=$CH_3$; 0.195 g, 0.584 mmol) is dissolved in 1.2 mL THF. Dicyclohexylcarbodiimide (0.127 g, 0.616 mmol) is added, followed by BOC-D-histidine-BOC-OH . 1 benzene (0.254 g, 0.586 mmol) and the mixture is stirred 2 hours at room temperature. Some THF (~2 mL) and ether (~2 mL) is added, and the solids filtered off. The filtrate is evaporated, and the residue taken up in a little methylene chloride and triturated with ether and pentane. The solids obtained are chromatographed on silica using methanol/methylene chloride to afford clean bis&-BOC 2 (0.207 g, 0.308 mmol; 53%). $^1$H-NMR (300 MHz, DMSO-d$_6$) δ 8.94 (s, 1H), 8.94–8.90 (m, 1H), 8.15 (s, 1H), 7.61–7.50 (m, 2H), 7.23 (s, 1H), 7.15 (d, J=8 Hz, 1H), 7.03 (dd, $J_{H-H}$=9 Hz, $J_{H-F}$=9 Hz, 1H), 5.01 (d, J=7 Hz, 2H), 4.75–4.63 (m,1H), 3.75–3.55 (m, 4H), 3.05–2.66 (m, 6H), 1.84 (s, 3H), 1.53 (s, 9H), 1.34 (s, 9H).

The above bis-BOC 2 (0.153 g, 0.228 mmol) is dissolved in 2 mL methylene chloride and 2 mL of trifluoroacetic acid is added. The mixture is allowed to stir at room temperature for 30 minutes. The solvents are pumped off, and the residue is dissolved in 3 mL methanol. 1N HCl (0.73 mL) is added, and the solution is stirred for 15 minutes. The mixture is pumped to dryness. Some methanol is added (1 mL), and the bis HCl salt triturated using ether and a little pentane. Compound 2·2 HCl is obtained (0.129 g, quant.) as an ivory solid. $^1$H-NMR (300 MHz, DMSO-d$_6$) δ 9.12 (s, 1H), 9.00–8.83 (m,1H), 8.95 (s, 1H), 8.45–8.30 (br m, 3H), 7.66–7.55 (m, 2H), 7.30 (s,1H), 7.07 (dd, $J_{H-H}$=9 Hz, $J_{H-F}$=9 Hz, 1H), 5.02 (d, J=7 Hz, 2H), 4.85–4.75 (m, 1H), 3.95–3.57 (m, 4H), 3.30–3.19 (m, 2H), 3.10–2.92 (m, 4H), 1.85 (s, 3H).

EXAMPLE 3

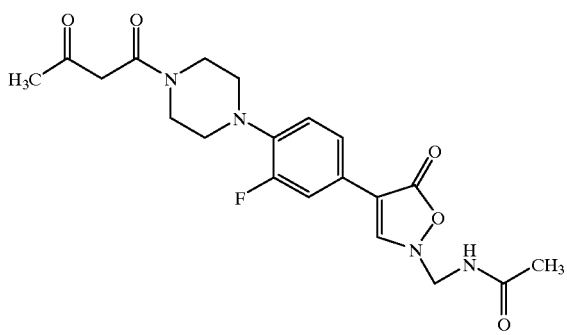

Synthesis of compound 3

Amine 41 ($R^3$=F, $R^2$=H, $R^1$=$CH_3$; 0.105 g, 0.314 mmol) is dissolved in 0.8 mL CH$_2$Cl$_2$ and 0.8 mL THF. Diketene (0.250 g, 2.98 mmol) is added and the mixture stirred 15 min at rt. The reaction is evaporated, and ether and pentane are added. The precipitate is collected to afford clean amide 3 (0.113 g, 0.270 mmol). $^1$H-NMR (300 MHz, DMSO-d$_6$) δ 8.98–8.90 (m, 2H), 7.63–7.52 (m, 2H), 7.07 (dd, $J_{H-H}$=9 Hz, $J_{H-F}$=9 Hz, 1H), 5.01 (d, J=7 Hz, 2H), 3.68–3.59 (m, 2H), 3.55–3.46 (m, 2H), 3.05–2.94 (m, 4H), 2.18 (s, 3H), 1.84 (s, 3H).

EXAMPLE 4

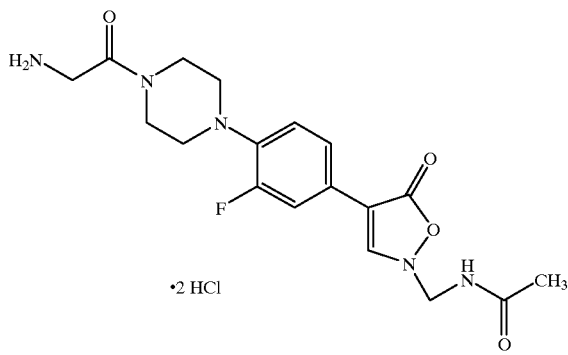

•2 HCl

Synthesis of compound 4

A. Amine 41 ($R^3$=F, $R^2$=H, $R^1$=CH$_3$; 0.146 g, 0.437 mmol) is dissolved in 0.9 mL THF. DCC (0.095 g, 0.460 mmol) is added, followed by BOC-glycine (0.077 g, 0.440 mmol), and the mixture is stirred 50 min at rt. THF (~2 mL) and ether (~2 mL) are added, and the insoluble material is filtered off. The filtrate is evaporated and the residue is chromatographed on silica gel using 15% methanol/methylene chloride as eluent. The fractions containing the product are evaporated to near dryness (~0.75 mL remaining), and ether and pentane are added to precipitate the product. The solids are collected, washed with pentane and pumped dry to afford BOC-4 (0.131 g, 0.267 mmol). $^1$H-NMR (300 MHz, DMSO-d$_6$) δ 8.98–8.90 (m, 2H), 7.63–7.52 (m, 2H), 7.08 (dd, $J_{H-H}$=9 Hz, $J_{H-F}$=9Hz, 1H), 6.80 (br t, J=7Hz, 1H), 5.01 (d, J=7Hz, 2H), 4.84 (d, J=7 Hz, 2H), 3.66–3.52 (m, 4H), 3.07–2.94 (m, 4H), 1.83 (s, 3H), 1.39 (s, 9H).

B. BOC-4 (0.099 g, 0.202 mmol) is treated with trifluoroacetic acid and HCl as described above in Example 1, part C. After trituration with methanol/ether there is obtained compound 4·2HCl (0.086 g, 0.201 mmol). $^1$H-NMR (300 MHz, DMSO-d$_6$) δ 8.98–8.92 (m, 2H), 8.14–8.04 (m, 3H), 7.63–7.53 (m, 2H), 7.07 (dd, $J_{H-H}$=9 Hz, $J_{H-F}$=9 Hz, 1H), 5.01 (d, J=7 Hz, 2H), 4.00–3.90 (m, 2H), 3.59–3.50 (m, 2H), 3.10–2.97 (m, 4H), 1.83 (s, 3H).

EXAMPLE 5

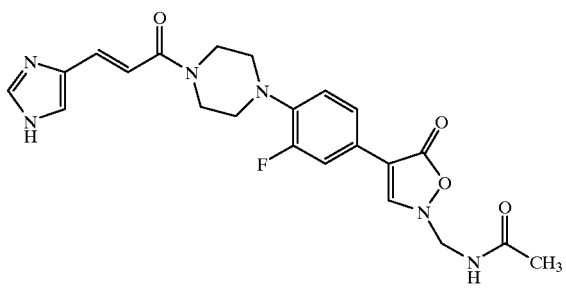

Synthesis of compound 6

TFA salt 32 ($R^3$=F, $R^2$=H, $R^1$=CH$_3$; 0.200 g, 0.430 mmol), N-methylmorpholine (0.38 mL, 3.44 mmol), urocanic acid (0.057 g, 0.430 mmol), and N-hydroxybenzotriazole (0.099 g, 0.650 mmol) are dissolved in 3 mL DMF. EDC (0.124 g, 0.650 mmol) is added, and the reaction is allowed to stir overnight at rt. The DMF is evaporated, and the residue is partitioned between 20% methanol/chloroform and half-saturated brine. The mixture is shaken and separated, and the aqueous is washed with 20% methanol/chloroform. The combined organic layer is washed with brine, dried (MgSO$_4$) and concentrated. The residue is triturated from chloroform/ether, and the crude solid is chromatographed on silica gel using methanol/CH$_2$Cl$_2$ (2% stepped up to 10%) to yield 6 (0.045 g, 0.099 mmol). $^1$H-NMR (300 MHz, DMSO-d$_6$) δ 8.98–8.92 (m, 2H), 7.86–7.28 (m, 5H), 7.15–6.99 (m, 2H), 5.01 (d, J=7 Hz, 2H), 3.83–3.67 (m, 4H), 3.12–2.97 (m, 4H), 1.83 (s, 3H).

EXAMPLE 6

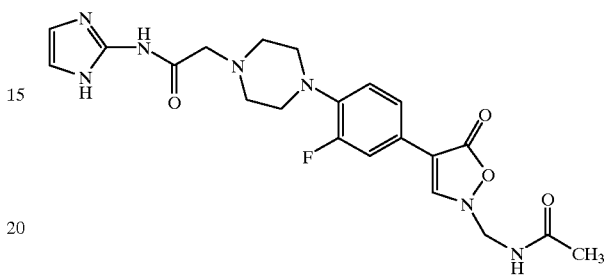

Synthesis of intermediates 38 and 39, and compound 10

A. t-Butyl bromoacetate (0.960 mL, 6.60 mmol) is suspended in 30 mL acetone. A catalytic amount of sodium iodide (~50 mg) is added, and the mixture stirred for 5 min. Triethylamine (1.80 mL, 13.2 mmol) is added followed by amine salt 32 ($R^3$=F, $R^2$=H, $R^1$=CH$_3$; 3.00 g, 6.60 mmol). The reaction is stirred 30 min at rt, and then evaporated. The residue is dissolved in 20% methanol/chloroform and partitioned with half-saturated brine. The mixture is shaken and separated, and the aqueous is washed with 20% methanol/chloroform. The combined organic layer is washed with brine, dried (MgSO$_4$) and concentrated to afford ester 38 ($R^3$=F, $R^2$=H, $R^1$=CH$_3$; 3.02 g, 6.48 mmol). $^1$H-NMR (300 MHz, DMSO-d$_6$) δ 8.96–8.90 (m, 2H), 7.60–7.50 (m, 2H), 7.06 (dd, $J_{H-H}$=9 Hz, $J_{H-F}$=9 Hz, 1H), 5.00 (d, J=7 Hz, 2H), 3.18 (br s, 2H), 3.07–2.98 (m, 4H), 2.71–2.61 (m, 4H), 1.83 (s, 3H), 1.42 (s, 9H).

B. The above ester 38 (3.02 g, 6.48 mmol), is dissolved in 10 mL methylene chloride and 10 mL TFA is added. The reaction mixture is stirred for 5 h at rt, and then an additional 10 mL of TFA is added and the reaction stirred another 15 h. The mixture is evaporated, and the residue triturated with CH$_2$Cl$_2$/ether to afford acid 39·1.3 TFA ($R^3$=F, $R^2$=H, $R^1$=CH$_3$; 3.41 g, quant.). $^1$H-NMR (300 MHz, DMSO-d$_6$) δ 8.99–8.91 (m, 2H), 7.65–7.56 (m, 2H), 7.13 (dd, $J_{H-H}$=9 Hz, $J_{H-F}$=9 Hz, 1H), 5.01 (d, J=7 Hz, 2H), 4.21 (br s, 2H), 4.03–3.50 (br m, 4H), 3.60–3.20 (br m, 4H), 1.83 (s, 3H).

C. Acid 39·1.3 TFA ($R^3$=F, $R^2$=H, $R^1$=CH$_3$; 0.200 g, 0.320 mmol), N-methylmorpholine (0.280 mL, 0.480 mmol), N-hydroxybenzotriazole hydrate (0.074 g, 0.480 mmol) and 2-aminoimidazole sulfate (0.049 g, 0.32 mmol) are dissolved in 3 mL DMF. EDC (0.093 g, 0.480 mmol) is added and the reaction stirred for 20 h. The reaction mixture is concentrated under vacuum, and the residue is diluted with 20% methanol/chloroform and poured into half-saturated aqueous sodium bicarbonate. The mixture is shaken and separated, and the organic phase is washed with brine, dried (MgSO$_4$) and evaporated. The residue is triturated with CHCl$_3$ and ether, and the solid is collected to provide amide 10 (0.106 g, 0.231 mmol). $^1$H-NMR (300 MHz, DMSO-d$_6$) δ 8.98–8.91 (m, 2H), 7.60–7.53 (m, 2H), 7.07 (dd, $J_{H-H}$=9 Hz, $J_{H-F}$=9 Hz, 1H), 6.80 (br s, 1H), 6.67 (br s, 1H), 5.00 (d, J=7 Hz, 2H), 4.58 (t, J=6 Hz, 1H), 3.27 (s, 2H), 3.13–3.00 (m, 4H), 2.76–2.65 (m, 4H), 1.84 (s, 3H).

EXAMPLE 7

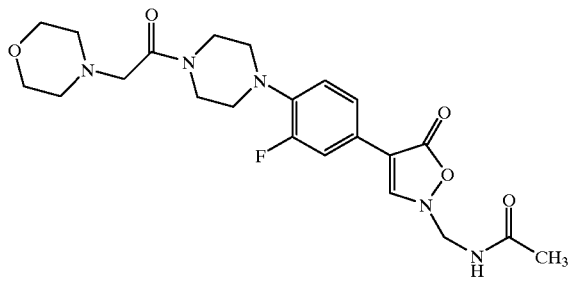

Synthesis of intermediate 34 and compound 14

A. TFA salt 32 ($R^3$=F, $R^2$=H, $R^1$=$CH_3$; 1.00 g, 2.20 mmol), is suspended in 9 mL acetone, and triethylamine (0.75 mL, 5.50 mmol) is added. Bromoacetyl chloride (0.18 mL, 2.20 mmol) is added, and a precipitate develops. The mixture is diluted with 20% methanol/chloroform and poured into 75% saturated brine. The mixture is shaken and separated, and the aqueous layer is extracted twice with 20% methanol/chloroform. The combined organic phase is washed with brine, dried ($MgSO_4$) and evaporated. The residue is taken up in ~10 mL methylene chloride and triturated with ether. The solid is collected and pumped dry to afford bromo amide 34 ($R^3$=F, $R^2$=H, $R^1$=$CH_3$; 0.630 g, 1.39 mmol). $^1$H-NMR (300 MHz, DMSO-$d_6$) δ 8.98–8.90 (m, 2H), 7.66–7.51 (m, 2H), 7.07 (dd, $J_{H-H}$=9 Hz, $J_{H-F}$=9 Hz, 1H), 5.00 (d, J=7 Hz, 2H), 4.43 (s, 2H), 3.67–3.58 (br m, 4H), 3.13–2.96 (br m, 4H), 1.84 (s, 3H).

B. Bromo amide 34 ($R^3$=F, $R^2$=H, $R^1$=$CH_3$; 0.200 g, 0.440 mmol) is dissolved in 2 mL acetone and a catalytic amount (~20 mg.) of sodium iodide is added. The mixture is stirred for 5 min, and then triethylamine (0.12 mL, 0.880 mmol) and morpholine (0.038 mL, 0.44 mmol) are added and the mixture stirred for 2 h at rt. The acetone is evaporated, and the material is diluted with 20% methanol/chloroform and poured into half-saturated brine. The mixture is shaken and separated, and the organic layer is dried ($MgSO_4$) and evaporated. The residue is taken up in methylene chloride and triturated with ether. The solid is collected and pumped dry to afford compound 14 (0.008 g, 0.017 mmol). $^1$H-NMR (300 MHz, DMSO-$d_6$) δ 8.98–8.90 (m, 2H), 7.63–7.51 (m, 2H), 7.08 (dd, $J_{H-H}$=9 Hz, $J_{H-F}$=9 Hz, 1H), 5.00 (d, J=7 Hz, 2H), 4.58 (t, J=6 Hz, 1H), 3.65–3.53 (m, 2H), 3.51–3.45 (m, 1H), 3.45–3.39 (m, 1H), 3.20 (s, 2H), 3.10–2.91 (m, 4H), 1.83 (s, 3H).

EXAMPLE 8

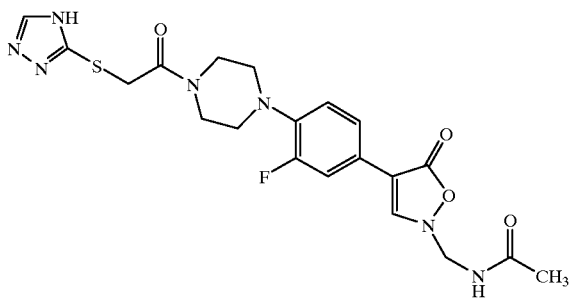

Synthesis of compound 18

2-Mercapto-1,3,4-triazole (0.045 g, 0.440 mmol) is dissolved in 2 mL acetone. Triethylamine (0.12 mL, 0.440 mmol) is added and the mixture stirred at rt for 5 min. Bromo amide 34 (see Example 7: $R^3$=F, $R^2$=H, $R^1$=$CH_3$; 0.200 g, 0.440 mmol) is added and the reaction is allowed to stir for 1 h. The mixture is evaporated, and the residue is diluted with ~30 mL 20% methanol/chloroform and poured into half-saturated brine. The mixture is shaken and separated, and the organic layer is washed with half-saturated brine. The aqueous layers are extracted with ~30 mL 20% methanol/chloroform and the combined organic phases are dried ($MgSO_4$) and evaporated. The residue is taken up in methylene chloride and triturated with ether. The solid is collected and pumped dry to afford compound 18 (0.091 g, 0.191 mmol). $^1$H-NMR (300 MHz, DMSO-$d_6$) δ 8.98–8.90 (m, 2H), 8.42 (br s,1H), 7.63–7.51 (m, 2H), 7.06 (dd, $J_{H-H}$=9 Hz, $J_{H-F}$=9 Hz, 1H), 5.01 (d, J=7 Hz, 2H), 4.25 (s, 2H), 3.75–3.60 (m, 4H), 3.12–2.95 (m, 4H), 1.84 (s, 3H).

EXAMPLE 9

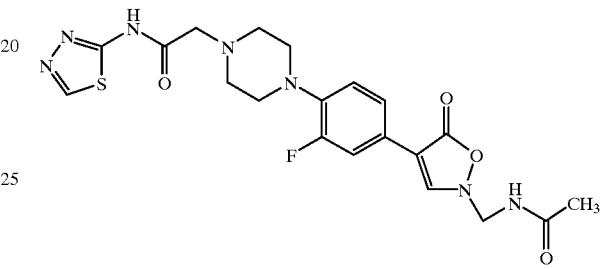

Synthesis of compound 22

Acid 39·1.3 TFA (See Step B of Example 6; $R^3$F, $R^2$=H, $R^1CH_3$; 0.200 g, 0.320 mmol), N-methylmorpholine (0.280 mL, 0.480 mmol), N-hydroxybenzotriazole hydrate (0.069 g, 0.450 mmol) and 2-amino-1,3,4-thiadiazole (0.038 g, 0.37 mmol) are dissolved in 3 mL DMF. EDC (0.086 g, 0.450 mmol) is added and the reaction stirred for 20 h. The reaction mixture is concentrated under vacuum, and the residue is diluted with 20% methanol/chloroform and poured into half-saturated aqueous sodium bicarbonate. The mixture is shaken and separated, and the organic phase is washed with brine, dried ($MgSO_4$) and evaporated. The residue is triturated with $CHCl_3$ and ether, and the solid is collected to provide amide 22 as a light orange solid (0.050 g, 0.105 mmol). $^1$H-NMR (300 MHz, DMSO-$d_6$) δ 9.19 (s, 1H), 8.95–8.90 (m, 1H), 8.92 (s, 1H), 7.61–7.50 (m, 2H), 7.05 (dd, $J_{H-H}$=7 Hz, $J_{H-F}$=7 Hz, 1H), 5.05 (d, J=8 Hz, 2H), 3.45 (s, 2H), 3.15–3.05 (br m, 4H), 2.75–2.65 (br m, 4H), 1.84 (s, 3H).

EXAMPLE 10

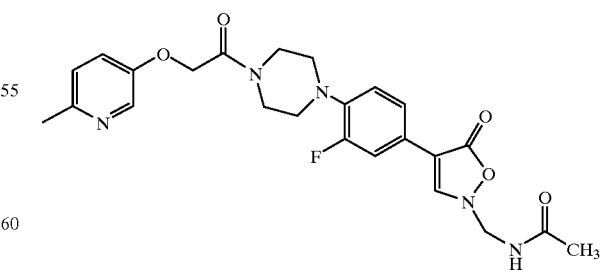

Synthesis of compound 25

6-Methyl-3-hydroxypyridine (0.048 g, 0.440 mmol) is dissolved in 3 mL DMF. Potassium t-butoxide (0.054 g, 0.480 mmol) is added and the mixture is stirred for 10 minutes at room temperature. Bromo amide 34 (see Example 7: $R^3$=F, $R^2$=H, $R^1$=CH$_3$; 0.200 g, 0.440 mmol) is added, followed by a catalytic amount of sodium iodide. The mixture is allowed to stir for 3 hours. The mixture is evaporated, and the residue is diluted with ~30 mL 20% methanol/chloroform and poured into half-saturated brine. The mixture is shaken and separated, and the organic layer is washed with half-saturated brine. The aqueous layers are extracted with ~30 mL 20% methanol/chloroform and the combined organic phases are dried (MgSO$_4$) and evaporated. Chromatography on silica gel using methanol/methylene chloride (2%–10% methanol) affords amide 25 (0.152 g, 0.314 mmol) as a white solid. $^1$H-NMR (300 MHz, DMSO-d$_6$) δ 8.96–8.91 (m, 2H), 8.17 (d, J=3 Hz, 1H), 7.65–7.57 (m, 2H), 7.28 (dd, J$_1$=8 Hz, J$_2$=3 Hz, 1H), 7.18 (d, J=8 Hz, 1H), 7.10 (dd, J$_{H-H}$=8 Hz, J$_{H-F}$=8 Hz, 1H), 5.10 (d, J=7 Hz, 2H), 4.95 (s, 2H), 3.65–3.59 (br m, 4H), 3.15–2.905 (br m, 4H), 2.39 (s, 3H), 1.83 (s, 3H).

EXAMPLE 11

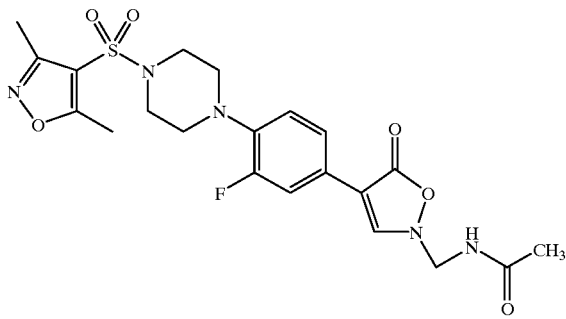

Synthesis of compound 26

Amine 41 ($R^3$=F, $R^2$=H, $R^1$=CH$_3$; 0.075 g, 0.225 mmol) is dissolved in 0.9 mL methylene chloride. Triethylamine (35 μL, 0.236 mmol) is added, followed by 3,5-dimethylisoxazole-4-sulfonyl chloride (0.044 g, 0.225 mmol), and the mixture is allowed to stir at room temperature for 4 days. The mixture is partitioned between methylene chloride and water. The organic phase is washed with water, then brine, and dried (MgSO$_4$) and evaporated. Sulfonamide 26 is obtained as a light yellow foam (0.093 g, 0.188 mmol). $^1$H-NMR (300 MHz, DMSO-d$_6$) δ8.94 (s, 1H), 8.95–8.91 (m, 1H), 7.63–7.50 (m, 2H), 7.08 (dd, J$_{H-H}$=9 Hz, J$_{H-F}$ 9 Hz, 1H), 5.01 (d, J=7 Hz, 2H), 3.26–3.05 (m, 8H), 2.66 (s, 3H), 2.48 (s, 3H), 1.84 (s, 3H).

EXAMPLE 12

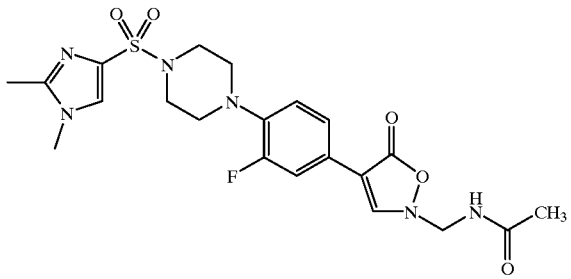

Synthesis of compound 27

Amine 41 ($R^3$=F, $R^2$=H, $R^1$=CH$_3$; 0.068 g, 0.202 mmol) is dissolved in 1 mL methylene chloride. Triethylamine (0.10 mL, 0.719 mmol) is added, followed by 4,5-dimethylimidazole-2-sulfonyl chloride (0.045 g, 0.231 mmol), and the mixture is allowed to stir at room temperature for 4 hours. The reaction mixture is partitioned between 20% methanol/chloroform and water. The organic phase is washed with brine, dried (MgSO$_4$), and evaporated. The solid was dissolved in a little methanol/methylene chloride and tritutrated with ether to afford sulfonamide 27 (0.077 g, 0.156 mmol) as a light brown solid. $^1$H-NMR (500 MHz, DMSO-d$_6$) δ 8.93 (s, 1H), 8.94–8.91 (m, 1H), 7.77 (s, 1H), 7.57–7.51 (m, 2H), 7.06 (dd, J$_{H-H}$=9 Hz, J$_{H-F}$=9 Hz, 1H), 5.00 (d, J=7 Hz, 2H), 3.62 (s, 3H), 3.26–2.95 (m, 8H), 2.33 (s, 3H), 1.83 (s, 3H).

EXAMPLE 13

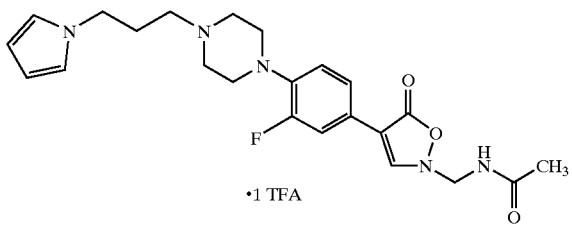

Synthesis of compound 30

Amine 41 ($R^3$=F, $R^3$=H, $R^1$=CH$_3$; 0.204 g, 0.610 mmol) is dissolved in 1.2 mL DMF. Sodium bicarbonate (0.155 g, 1.84 mmol) is added, followed by 1-(3-bromopropyl)-pyrrole (0.160 g, 0.852 mmol), and the mixture is allowed to stir overnight at room temperature. The mixture is partitioned between 20% methanol/chloroform and half-saturated brine. The organic layer is dried (MgSO$_4$), and evaporated. The residue is dissolved in a little methanol/methylene chloride and triturated with ether. A white solid precipitates that turns dark brown upon filtration. The sticky material was eluted off the filter paper with methanol/methylene chloride, and the solvents evaporated. The material is then purified by preparatory reverse-phase HPLC to afford 30·1.0 TFA (0.020 g, 0.036 mmol) as a brown oil. $^1$H-NMR (500 MHz, CDCl$_3$, partial) δ 8.23 (s, 1H), 7.50–7.39 (m, 2H), 6.90 (dd, J$_{H-H}$=9 Hz, J$_{H-F}$=9 Hz, 1H), 6.64–6.62 (br m, 2 H), 6.18–6.16 (br m, 2 H), 5.06 (d, J=7 Hz, 2H), 4.03 (t, J=6 Hz, 2 H), 3.33–3.22 (m, 4H), 3.00–2.90 (m, 4H), 2.32–2.26 (m, 2H), 1.97 (s, 3H).

EXAMPLE 14

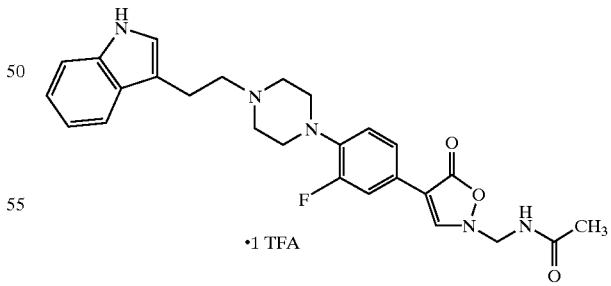

Synthesis of compound 31

Amine 41 ($R^3$=F, $R^2$=H, $R^1$=CH$_3$; 0.098 g, 0.294 mmol) is dissolved in 1 mL DMF. Sodium bicarbonate (0.079 g, 0.938 mmol) is added, followed by 3-(1-bromoethyl)-indole (0.074 g, 0.330 mmol), and the mixture is allowed to stir for five days at room temperature. The mixture is partitioned between 20% methanol/chloroform and half-saturated brine. The organic layer is dried (MgSO$_4$), and evaporated. The residue is dissolved in a little methanol/methylene chloride and triturated with ether. The solids are removed by filtration, and the filtrate is concentrated and purified by reverse-phase preparatory HPLC to afford 31 . 1.0 TFA as a yellow oil (0.051 g, 0.086 mmol). H-NMR (500 MHz, CDCl$_3$, partial) δ 8.63 (s, 1H), 7.61 (d, J=8 Hz, 12H), 7.59–7.51 (m, 2H), 7.37 (d, J=8 Hz, 1H), 7.17–7.03 (m, 3H), 1.93 (s, 3H).

We claim:

1. A compound of formula I

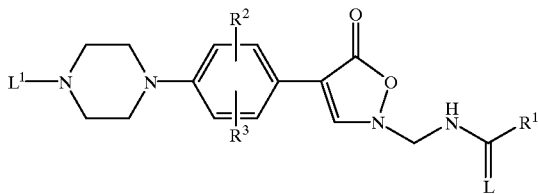

or a pharmaceutically acceptable salt thereof, wherein:

L is oxygen or sulfur;

L$^1$ is selected from the group consisting of: R$^4$—(CH$_2$)$_m$—CR$^5$(NR$^6$R$^7$)C(O)—, R$^8$R$^9$N—(CH$_2$)$_n$—C(O)—, C$_{1-6}$alkylC(O)CH$_2$C(O)—, R$^{10}$—X—CH$_2$C(O)—, R$^{10}$—CH=CH—C(O)—, R$^{10}$—NHC(O)CH$_2$—, R$^{10}$—(CH$_2$)$_p$— and R$^{10}$—S(O)$_2$—;

m is 0 or an integer from 1 to 4;

n is an integer from 1 to 4;

p is an integer from 2 to 6;

X is selected from the group consisting of: a bond, sulfur, oxygen, NH and N(C$_{1-4}$alkyl);

R$^1$ is selected from the group consisting of: hydrogen, C$_{1-8}$alkyl, C$_{3-6}$cycloalkyl and C$_{1-8}$alkoxy, said C$_{1-8}$alkyl optionally substituted with one or more fluoro, chloro, hydroxy, C$_{1-8}$alkoxy or C$_{1-8}$acyloxy;

R$^2$ and R$^3$ are each independently selected from the group consisting of: hydrogen, halogen, hydroxy, nitro, amino, cyano, C$_{1-6}$alkyl, C$_{1-6}$alkoxy and trifluoromethyl;

R$^4$ is selected from the group consisting of: hydrogen, hydroxy, C$_{1-6}$thioalkoxy, imidazolyl, indolyl, —CO$_2$H and —NHC(=NH)NH$_2$;

R$^5$ is hydrogen or C$_{1-6}$alkyl; or R$^4$ and R$^5$ taken together can be —CH$_2$— when m is 1;

R$^6$ and R$^7$ are each independently selected from hydrogen or C$_{1-6}$alkyl; or R$^4$ and R$^6$ taken together can be —(CH$_2$)$_q$— when m is 1 and wherein q is 2 or 3;

R$^8$ and R$^9$ are each independently selected from hydrogen or C$_{1-6}$alkyl; or R$^8$ and R$^9$ taken together with the nitrogen to which they are attached are morpholin-4-yl, piperazin-1-yl, piperidin-1-yl or —NHC(=NH)NH$_2$;

R$^{10}$ is heteroaryl, said heteroaryl selected from the group consisting of imidazolyl, benzoimidazolyl, thienyl, benzothienyl, furanyl, oxazolyl, isoxazolyl, thiazolyl, isothiazolyl, indolyl, pyridinyl, pyrimidinyl, pyrazinyl, pyrolyl, thiadiazolyl, oxadiazolyl, triazolyl, triazinyl and tetrazolyl, and said heteroaryl optionally substituted with one to three same or different amino, hydroxy, halogen, C$_{1-6}$alkyl, morpholin-4-yl, piperazin-1-yl, piperidin-1-yl, phenyl, —CO$_2$H or —CO$_2$C$_{1-6}$alkyl; and provided R$^4$ is hydrogen or C$_{1-6}$alkyl and R$^5$ is C$_{1-6}$alkyl when m is 0.

2. A compound of claim 1, of the formula Ia

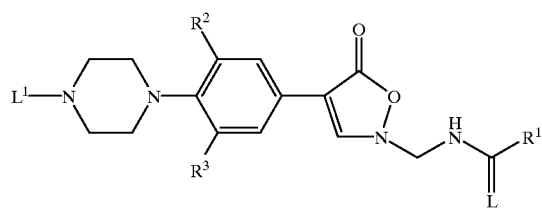

or a pharmaceutically acceptable salt thereof, wherein:

L is oxygen;

R$^1$ is C$_{1-8}$alkyl; and

R$^2$ and R$^3$ are each independently hydrogen or halogen.

3. A compound of claim 2, or a pharmaceutically acceptable salt thereof, wherein:

R$^1$ is methyl; and

R$^2$ and R$^3$ are each independently hydrogen or fluoro.

4. A compound of claim 3, or a pharmaceutically acceptable salt thereof, wherein:

R$^2$ is hydrogen;

R$^3$ is fluoro; and

L$^1$ is R$^4$—(CH$_2$)$_m$—CR$^5$(NR$^6$R$^7$)C(O)— or R$^8$R$^9$N—(CH$_2$)$_n$—C(O)—.

5. A compound of claim 4, or a pharmaceutically acceptable salt thereof, wherein:

L$^1$ is R$^4$—(CH$_2$)$_m$—CR$^5$(NR$^6$R$^7$)C(O)—;

R$^4$ is selected from the group consisting of hydrogen, hydroxy, thiomethoxy, 1H-imidazol-4-yl, indolyl, —CO$_2$H and —NHC(=NH)NH$_2$;

R$^5$ is hydrogen or C$_{1-6}$alkyl, said C$_{1-6}$alkyl selected from the group consisting of methyl, ethyl, propyl, isopropyl and 2-methylpropyl; or R$^4$ and R$^5$ taken together can be —CH$_2$— when m is 0;

R$^6$ is hydrogen or methyl; or R$^4$ and R$^6$ taken together can be —(CH$_2$)$_q$— when m is 1 and wherein q is 2 or 3;

R$^7$ is hydrogen or C$_{1-6}$alkyl, said C$_{1-6}$alkyl selected from the group consisting of methyl, ethyl, propyl and isopropyl.

6. A compound of claim 5, or a pharmaceutically acceptable salt thereof, wherein:

R$^4$ and R$^6$ taken together are —(CH$_2$)$_q$— wherein q is 2 or 3; and m is 1.

7. A compound of claim 5, or a pharmaceutically acceptable salt thereof, wherein:

R$^4$ is hydrogen;

m is 0;

R$^5$ is C$_{1-6}$alkyl, said C$_{1-6}$alkyl selected from the group consisting of methyl, ethyl, propyl, isopropyl and 2-methylpropyl; and R$^6$ and R$^7$ are each independently hydrogen or methyl.

8. A compound of claim 5, or a pharmaceutically acceptable salt thereof, wherein:

R$^4$ is selected from the group consisting of hydroxy, thiomethoxy, 1H-imidazol-4-yl, —CO$_2$H and —NHC(=NH)NH$_2$;

R$^5$ is hydrogen;

R$^6$ and R$^7$ are hydrogen; and m is an integer from 1 to 3.

9. A compound of claim 4, or a pharmaceutically acceptable salt thereof, wherein:

$L^1$ is $R^8R^9N-(CH_2)_n-C(O)-$;

$R^8$ and $R^9$ are each independently selected from hydrogen or $C_{1-6}$alkyl; said $C_{1-8}$alkyl selected from the group consisting of methyl, ethyl and propyl; or $R^8$ and $R^9$ taken together with the nitrogen to which they are attached are morpholin-4-yl or $-NHC(=NH)NH_2$; and n is an integer from 1 to 3.

10. A compound of claim 3, or a pharmaceutically acceptable salt thereof, wherein:

$L^1$ is $C_{1-6}$alkylC(O)CH$_2$C(O)—;

$R^2$ is hydrogen; and $R^3$ is fluoro.

11. A compound of claim 3, or a pharmaceutically acceptable salt thereof, wherein:

$L^1$ is $R^{10}-X-CH_2C(O)-$;

X is selected from the group consisting of a bond, sulfur, oxygen and NH;

$R^2$ is hydrogen; and $R^3$ is fluoro.

12. A compound of claim 11, or a pharmaceutically acceptable salt thereof, wherein:

$R^{10}$ is heteroaryl, said heteroaryl selected from the group consisting of imidazolyl, benzoimidazolyl, pyridinyl, pyrimidinyl, thiadiazolyl, thiazolyl, tetrazolyl, and triazolyl, and said heteroaryl optionally substituted with one to three same or different amino, hydroxy, $C_{1-6}$alkyl, phenyl or $-CO_2C_{1-6}$alkyl.

13. A compound of claim 3, or a pharmaceutically acceptable salt thereof, wherein:

$L^1$ is $R^{10}-CH=CH-C(O)-$;

$R^2$ is hydrogen; and $R^3$ is fluoro.

14. A compound of claim 3, or a pharmaceutically acceptable salt thereof, wherein:

$L^1$ is $R^{10}-NHC(O)CH_2-$;

$R^2$ is hydrogen; and $R^3$ is fluoro.

15. A compound of claim 14, or a pharmaceutically acceptable salt thereof, wherein:

$R^{10}$ is heteroaryl, said heteroaryl selected from the group consisting of triazolyl, thiadiazolyl and imidazolyl, and said heteroaryl optionally substituted with one $C_{1-6}$alkyl or morpholin-4-yl.

16. A compound of claim 3, or a pharmaceutically acceptable salt thereof, wherein:

$L^1$ is $R^{10}-(CH_2)_p-$;

$R^2$ is hydrogen; and $R^3$ is fluoro.

17. A compound of claim 16, or a pharmaceutically acceptable salt thereof, wherein:

$R^{10}$ is pyrol-1-yl or indol-3-yl; and p is 2 or 3.

18. A compound of claim 3, or a pharmaceutically acceptable salt thereof, wherein:

$L^1$ is $R^{10}-S(O)_2-$; and $R^2$ is hydrogen.

19. A compound of claim 18, or a pharmaceutically acceptable salt thereof, wherein:

$R^{10}$ is heteroaryl, said heteroaryl selected from imidazolyl or isoxazolyl, and said heteroaryl optionally substituted with one or two $C_{1-6}$alkyl.

20. A compound of claim 1, or a pharmaceutically acceptable salt thereof, selected from the group consisting of:

N-[4-(4-{4-[2-Amino-3-(1H-indol-3-yl)-propionyl]-piperazin-1-yl}-3-fluoro-phenyl)-5-oxo-5H-isoxazol-2-ylmethyl]-acetamide;

N-[4-(4-{4-[2-Amino-3-(1H-imidazol-4-yl)-propionyl]-piperazin-1-yl}-3-fluoro-phenyl)-5-oxo-5H-isoxazol-2-ylmethyl]-acetamide;

N-(4-{3-Fluoro4-[4-(3-oxo-butyryl)-piperazin-1-yl]-phenyl}-5-oxo-5H-isoxazol-2-ylmethyl)-acetamide;

N-(4-{4-[4-(2-Amino-acetyl)-piperazin-1-yl]-3-fluoro-phenyl}-5-oxo-5H-isoxazol-2-ylmethyl)-acetamide;

N-(4-{3-Fluoro-4-[4-(2-1H-imidazol-4-yl-acetyl)-piperazin-1-yl]-phenyl}-5-oxo-5H-isoxazol-2-ylmethyl)-acetamide;

N-(4-{3-Fluoro-4-[4-(3-1H-imidazol4-yl-acryloyl)-piperazin-1-yl]-phenyl}-5-oxo-5H-isoxazol-2-ylmethyl)-acetamide;

N-[4-(4-{4-[2-(1H-Benzoimidazol-2-ylsulfanyl)-acetyl]-piperazin-1-yl}-3-fluoro-phenyl)-5-oxo-5H-isoxazol-2-ylmethyl]-acetamide;

N-[4-(3-Fluoro4-{4-[2-(4-methyl-4H-[1, 2, 4]triazol-3-ylsulfanyl)-acetyl]-piperazin-1-yl}-phenyl)-5-oxo-5H-isoxazol-2-ylmethyl]-acetamide;

2-[2-(4-{4-[2-(Acetylamino-methyl)-5-oxo-2,5-dihydro-isoxazol-4-yl]-2-fluoro-phenyl}-piperazin-1-yl)-2-oxo-ethylsulfanyl]-1H-imidazole-4-carboxylic acid ethyl ester;

2-(4-{4-[2-(Acetylamino-methyl)-5-oxo-2,5-dihydro-isoxazol-4-yl]-2-fluoro-phenyl}-piperazin-1-yl)-N-(1H-imidazol-2-yl)-acetamide;

N-[4-(3-Fluoro-4-{4-[2-(5-phenyl-4H-[1, 2, 4]triazol-3-ylsulfanyl)-acetyl]-piperazin-1-yl}-phenyl)-5-oxo-5H-isoxazol-2-ylmethyl]-acetamide;

N-[4-(3-Fluoro-4-{4-[2-(1-methyl-1H-imidazol-2-ylsulfanyl)-acetyl]-piperazin-1-yl}-phenyl)-5-oxo-5H-isoxazol-2-ylmethyl]-acetamide;

N-[4-(3-Fluoro-4-{4-[2-(pyrimidin-2-ylsulfanyl)-acetyl]-piperazin-1-yl}-phenyl)-5-oxo-5H-isoxazol-2-ylmethyl]-acetamide;

N-(4-{3-Fluoro-4-[4-(2-morpholin-4-yl-acetyl)-piperazin-1-yl]-phenyl}-5-oxo-5H-isoxazol-2-ylmethyl)-acetamide;

N-[4-(3-Fluoro-4-{4-[2-(5-methyl4H-[1, 2, 4]triazol-3-ylsulfanyl)-acetyl]-piperazin-1-yl}-phenyl)-5-oxo-5H-isoxazol-2-ylmethyl]-acetamide;

N-[4-(4-{4-[2-(5-Amino-[1, 3, 4]thiadiazol-2-ylsulfanyl)-acetyl]-piperazin-1-yl}-3-fluoro-phenyl)-5-oxo-5H-isoxazol-2-ylmethyl]-acetamide;

N-[4-(3-Fluoro-4-{4-[2-([1, 3, 4]thiadiazol-2-ylsulfanyl)-acetyl]-piperazin-1-yl}-phenyl)-5-oxo-5H-isoxazol-2-ylmethyl]-acetamide;

N-[4-(3-Fluoro-4-{4-[2-(4H-[1, 2, 4]triazol-3-ylsulfanyl)-acetyl]-piperazin-1-yl}-phenyl)-5-oxo-5H-isoxazol-2-ylmethyl]-acetamide;

N-[4-(3-Fluoro-4-{4-[2-(thiazol-2-ylsulfanyl)-acetyl]-piperazin-1-yl}-phenyl)-5-oxo-5H-isoxazol-2-ylmethyl]-acetamide;

N-[4-(3-Fluoro-4-{4-[2-(1-methyl-1H-tetrazol-5-ylsulfanyl)-acetyl]-piperazin-1-yl}-phenyl)-5-oxo-5H-isoxazol-2-ylmethyl]acetamide;

N-[4-(3-Fluoro4-{4-[2-(1H-imidazol-2-ylsulfanyl)-acetyl]-piperazin-1-yl}-phenyl)-5-oxo-5H-isoxazol-2-ylmethyl]-acetamide;

2-(4-{4-[2-(Acetylamino-methyl)-5-oxo-2,5-dihydro-isoxazol-4-yl]-2-fluoro-phenyl}piperazin-1-yl)-N-[1,3,4]thiadiazol-2-yl-acetamide;

N-[4-(3-Fluoro-4-{4-[2-(5-methyl-[1, 3, 4]thiadiazol-2-ylsulfanyl)-acetyl]-piperazin-1-yl}-phenyl)-5-oxo-5H-isoxazol-2-ylmethyl]-acetamide;

N-[4-(3-Fluoro-4-{4-[2-(5-hydroxy-4-methyl-4H-[1,2,4]triazol-3-ylsulfanyl)-acetyl]-piperazin-1-yl}-phenyl)-5-oxo-5H-isoxazol-2-ylmethyl]acetamide;

N-[4-(3-Fluoro-4-{4-[2-(6-methyl-pyridin-3-yloxy)-acetyl]-piperazin-1-yl}-phenyl)-5-oxo-5H-isoxazol-2-ylmethyl]-acetamide;

N-(4-{4-[4-(3,5-Dimethyl-isoxazole-4-sulfonyl)-piperazin-1-yl]-3-fluoro-phenyl}-5-oxo-5H-isoxazol-2-ylmethyl)-acetamide;

N-(4-{4-[4-(1,2-Dimethyl-1H-imidazole-4-sulfonyl)-piperazin-1-yl]-3-fluoro-phenyl}-5-oxo-5H-isoxazol-2-ylmethyl)-acetamide;

N-(4-{3-Fluoro-4-[4-(1-methyl-1H-imidazole-4-sulfonyl)-piperazin-1-yl]-phenyl}-5-oxo-5H-isoxazol-2-ylmethyl)-acetamide;

N-(4-{4-[4-(1-Methyl-1H-imidazole-4-sulfonyl)-piperazin-1-yl]-phenyl}-5-oxo-5H-isoxazol-2-ylmethyl)-acetamide;

N-(4-{3-Fluoro-4-[4-(3-pyrrol-1-yl-propyl)-piperazin-1-yl]-phenyl}-5-oxo-5H-isoxazol-2-ylmethyl)-acetamide; and N-[4-(3-Fluoro-4-{4-[2-(1H-indol-3-yl)-ethyl]-piperazin-1-yl}-phenyl)-5-oxo-5H-isoxazol-2-ylmethyl]-acetamide.

21. A pharmaceutical composition comprising a compound of any of claims 1–20 in admixture with a pharmaceutically acceptable adjuvant, diluent or carrier.

22. A method of treating a bacterial infection in a mammal which comprises administering a therapeutically effective amount of a compound of any of claims 1–20 to a mammal in need thereof.

* * * * *